US009057079B2

(12) United States Patent
Williams et al.

(10) Patent No.: US 9,057,079 B2
(45) Date of Patent: Jun. 16, 2015

(54) EXPRESSION ELEMENTS

(75) Inventors: Steven G. Williams, Cheshire (GB);
Robert L. Crombie, Melbourne (AU);
Kai S. Lipinski, Staffordshire (GB);
Alistair S. Irvine, Derbyshire (GB)

(73) Assignee: EMD Millipore Corporation, Billerica, MA (US)

( * ) Notice: Subject to any disclaimer, the term of this patent is extended or adjusted under 35 U.S.C. 154(b) by 2811 days.

(21) Appl. No.: 10/543,792

(22) PCT Filed: Feb. 2, 2004

(86) PCT No.: PCT/GB2004/000387
§ 371 (c)(1),
(2), (4) Date: Jun. 13, 2006

(87) PCT Pub. No.: WO2004/067701
PCT Pub. Date: Aug. 12, 2004

(65) Prior Publication Data
US 2008/0222742 A1    Sep. 11, 2008

(30) Foreign Application Priority Data

Feb. 1, 2003  (GB) .................................. 0302330.6
Apr. 12, 2003  (GB) .................................. 0308503.2
Sep. 5, 2003  (GB) .................................. 0320824.6

(51) Int. Cl.
| C12N 15/00 | (2006.01) |
| C12N 7/00 | (2006.01) |
| C12N 7/01 | (2006.01) |
| C12P 19/34 | (2006.01) |
| C12N 15/85 | (2006.01) |
| A61K 48/00 | (2006.01) |

(52) U.S. Cl.
CPC .................. *C12N 15/85* (2013.01); *A61K 48/00* (2013.01); *C12N 2830/46* (2013.01); *A01K 2217/05* (2013.01); *C12N 2800/108* (2013.01)

(58) Field of Classification Search
None
See application file for complete search history.

(56) References Cited

U.S. PATENT DOCUMENTS

| 5,583,009 | A  | 12/1996 | Palmiter et al. |
| 5,610,053 | A  | 3/1997  | Chung et al.    |
| 6,689,606 | B2 | 2/2004  | Antoniou et al. |
| 6,881,556 | B2 | 4/2005  | Antoniou et al. |
| 6,949,361 | B2 | 9/2005  | Antoniou et al. |
| 6,964,951 | B2 | 11/2005 | Antoniou et al. |
| 7,442,787 | B2 | 10/2008 | Antoniou et al. |

FOREIGN PATENT DOCUMENTS

| WO | WO94/13273    | 6/1994  |
| WO | WO95/33841    | 12/1995 |
| WO | WO98/07876    | 2/1998  |
| WO | WO 00/05393   | 2/2000  |
| WO | WO 02/24930   | 3/2002  |
| WO | WO 0224930    | 3/2002  |
| WO | WO 02/081677  | 10/2002 |
| WO | WO 02/099089  | 12/2002 |
| WO | WO 03/006607  | 1/2003  |

OTHER PUBLICATIONS

Cuadrado et al., 2001, EMBO Reports, 21: 586-592.*
Monohan et al., 2000, Molecular Medicine Today, 6: 443-440.*
Bitnaite et al., 1991, Nucleic Acids Research, 19: 5076.*
Needham et al., "Further development of the locus control region/murine erthroleukemia expression system:high level expression and characterization of recombinant human calcitonin receptor", Protein Expression and Purification, 1995, 6:124-131.*
Antoniou M et al., "Transgenes Encompassing Dual-Promoter CpG Islands from the Human TBP and HNRPA2B1 Loci are Resistant to Heterochromat in-mediated Silencing," Genomics, Academic Press, San Diego, US, pp. 269-279, XP004442995.
Kozu T. et al., "Structure and Expression of the Gene (HNRPA2B1) Encoding the Human HNRNP Protein A2/B1", Genomics, Academic Press, San Diego, US, vol. 25, No. 2, Jan. 20, 1995, pp. 365-371, XP000870070.
Huxley C. et al, "The Mouse Surfeit Locus Contains a Cluster of Six Genes Associated with Four CPG-Rich Islands in 32 Kilobases of Genomic DNA", Molecular Cell Biology, vol. 10, No. 2, Feb. 1990, pp. 605-614, XP000870104.
Antoniou M et al., "Transgenes Encompassing Dual-Promoter CpG Islands from the Human TBP and HNRPA2B1 Loci are Resistant to Heterochromat in-mediated Silencing," Genomics, Academic Press, San Diego, US, pp. 269-279, XP004442995, 2003.
PCT International Search Report for international application No. PCT/GB2004/000387, 6 pages.
Bonifer, "Long-distance chromatin mechanisms controlling tissue-specific gene locus activation", Gene, 238(2):277-289, Oct. 1999.
Peter Gunning et al., a human β-actin expression vector system directs high-level accumulation of antisense transcripts, Proc. Natl. Acad. Sci, vol. 84, pp. 4831-4835, Jul. 1987.
Corcoran et al., "High-level regulated expression of the human G6PD gene in transgenic mice", Gene, 173(2):241-246, Sep. 1996.
Biamonti et al., "Two homologous genes, originated by duplication, encode the human hnRNP proteins A2 and A1", Nucl. Acids Res., 22(11):1996-2002, Jun. 1994.
Genbank Accession No. U09120, National Library of Medicine, accessed by PTO, Jul. 5, 2000, Dec. 1994.
Genbank Accession No. D28877, National Library of Medicine, accessed by PTO, Jul. 5, 2000, Feb. 1999.
Genbank Accession No. AL031259, version AL031259.7 GI:3676176, accessed by PTO, Jul. 13, 2000, Sep. 1998.
Chalut et al., "Genomic structure of the human TATA-box-binding protein (TBP)", Gene, 161 (2):277-282, Aug. 1995.

(Continued)

*Primary Examiner* — Nita M Minnifield
(74) *Attorney, Agent, or Firm* — EMD Millopore Corporation

(57) ABSTRACT

The invention relates to improved genetic elements providing high levels of expression of operably-linked genes in a variety of tissues. In particular, fragments of unmethylated, CpG islands of less than 2 kb are shown to provide enhanced transgene expression and have advantages in terms of vector construction and cloning capacity.

13 Claims, 25 Drawing Sheets

(56) References Cited

OTHER PUBLICATIONS

Foulds et al., "Analysis of the human TATA binding protein promoter and identification of an Ets site critica for activity", Nucl. Acids Res., 25(12):2485-2494, Jun. 1997.

Chung et. al.; Characterization of the chicken β-globin insulator, 1997, Proc. Natl. Acad. Sci. vol. 94: 575-580.

Crane-Robinson, C. et al., "Chromosomal mapping of core histone acetylation by immunoselection," Methods, 1997, 12(1), 48-56 (summary only).

DiBartolomeis, S.M. et al., "A superfamily of *Drosophila* satellite related (SR) DNA repeats restricted to the X chromosome euchromatin," Nucl. Acids Res., 1992, 20(5), 1113-1116.

Duhig, T. et al., "The Human Surfeit Locus," Genomics, 1998, 52, 72-78.

Ellis, J. et al., "A dominant chromatin-opening activity in 5' hypersensitive site 3 of the human β-globin locus control region," EMBO J., 1996, 15(3), 562-568.

Ellis, J. et al., "Evaluation of β-globin gene therapy constructs in single copy transgenic mice," Nucl. Acids Res., 1997, 26(6), 1296-1302.

Gaston, K. et al., "CpG methylation has differential effects on the binding of YY1 and ETS proteins to the bi-directional promoter of the Surf-1 and Surf-2 genes," Nucl. Acids Res., 1995, 23(6), 901-909.

Gaston, K. et al., "YY1 is involved in the regulation of the bi-directional promotor of the Surf-1 and Surf-2 genes," FEBS Letts., 1994, 347, 289-294.

Garson, K. et al., "Surf5: A Gene in the Tightly Clustered Mouse Surfeit Locus is Highly Conserved and Transcribed Divergently from the rpL7a (Surf 3) Gene," Genomics, 1996, 30, 163-170.

Gavalas, A. et al., "Analysis of the chicken GPAT/AIRC bidirectional promoter for de novo purine nucleotide synthesis," J. Biol. Chem., 1995, 270(5), 2403-2410.

Lavia, P. et al., "Coincident start sites for divergent transcripts at a randomly selected CpG-rich island of mouse," EMBO J., 1987, 6, 2773-2779.

Palmiter, "The elusive function of metallothioneins," Proc. Natl. Acad. Sci. USA, 1998, 95, 8428-8430.

Talbot, D. et al., "The 5' flanking region of the rat LAP (C/EBPβ) gene can direct high-level, position-independent, copy number-dependent expression in multiple tissues in transgenic mice," Nucl. Acids Res., 1994, 22(5), 756-766.

Williams, T.J. et al., "The MES-1 Murine Enhancer Element is Closely Associated with the Heterogeneous 5' Ends of Two Divergent Transcription Units," Mol. Cell. Biol., 1986, 6(12), 4558-4569.

Winston, J. H. et al., "An intron 1 regulatory region from the murine adenosine deaminase gene can activate heterologous promoters for ubiquitous expression in transgenic mice," Som. Cell Mol. Genet., 1996, 22, 261-278.

Festenstein, R., et al., "Locus control region function and heterochromatic-induced position effect variegation," Science, 1996, 271(23), 1123-1125.

Gavalas, A., et al., "Coexpression of two closely linked avian genes for purine nucleotide synthesis from a bidirectional promoter," Mol. Cell Biol., 1983, 13(8), 4784-4792.

Huxley, C., et al., "The mouse surfeit locus contains a cluster of six genes associated with four Gp G-rich islands in 32 kilobases of genomic DNA," Mol. Cell Biol., 1990, 10(2), 605-614.

Ohbayashi, T., et al., "Promoter structure of the mouse TATA-binding protein (TBP) gene," Biochem. Biophys. Res. Commun., 1996, 225(1), 275-280.

Ryan M.T., et al., "The genes encoding mammalian chaperonin 60 and chaperonin 10 are linked head-to-head and share a bidirectional promoter," Gene: An International J on Genes and Genomes, 1997, 196(1-2), 9-17.

Ursini, et al., 1990, High levels of transcription driven by a 400 by segment of the human G6PD promotor, Biochem. Biophys. Res. Commun., 170:1203-1209.

Larsen, F. et al., "CpG Islands as Gene Markers in the Human Genome," Genomics, 1992, 13:1095-1107.

Recillas-Targa, F. et al., "Positional enhancer-blocking activity of the chicken β-globin insulator in tranciently transfected cells," Proc. Natl. Acad. Sci. USA, 1999, 96(25):14354-14359.

Ng et al., "Evolution of the Functional Human β-Actin Gene and Its MultiPseudogene Family: Conservation of Noncoding Regions and Chromosomal Dispersion of Pseudogenes," Mol. Cell. Biol., vol. 5, 1985, pp. 2720-2732.

Bell, A.C. & Felsenfield, G., "Stopped at the border: boundaries and insulators" Curr. Opin. Genet. Dev.,1999, 9, 191-198.

Sabbattini, P., Georgiou, A., Sinclaire, C. & Dillon, N., "Analysis of mice with single and multiple copies of transgenes reveals a novel arrangement for the .lambda.5-V-preBI locus control region" Mol. Cell. Biol, 1999,19, 671-679.

M. Garidiner-Garden et al., CpG Islands in Vertebrate Genomes, J. Mol. Biol. 196, 261-282, 1987.

Cheng, L., et al., "A GFP reporter system to assess gene transfer and expression in human hematopoietic progenitor cells," Gene Therapy, 4:1013-1022, (1997).

Cheng, L., et al., "Sustained Gene Expression in Retrovirally Transduced, Engrafting Human Hematopoietic Stem Cells and Their Lympho-Myeloid Progeny," Blood, 92(1):83-92, (Jul. 1, 1998).

Elwood, N.J., et al., "Retroviral Transduction of Human Progenitor Cells: Use of Granulocye Colony-Stimulating Factor Plus Stem Cell Factor to Mobilize Progenitor Cells In Vivo and Stimulation by Flt3/Flk-2 Ligand In Vitro," Blood, 88(12):4452-4462, (Dec. 15, 1996).

Lu, L., et al., "High Efficiency Retroviral Mediated Gene Trnasduction into Single Isolated Immature and Replatable CD34.sup.3+ Hematopoietic Stem/Progenitor Cells from Human Umbilical Cord Blood ," J. Exp. Med., 178:2089-2096, (Dec. 1993).

Whitwam, T., et al., "Retroviral Marking of Canine Bone Marrow: Long-Term, High-Level Expression of Human Interleukin-2 Receptor Common Gamma Chain in Canine Lymphocytes," Blood, 92(5):1565-1575, (Sep. 1, 1998).

Antequera, F. & Bird, A., "Number of CpG islands and genes in human and mouse" Proc. Natl. Acad. Sci. USA, 1993, 90, 11995-11999.

Bird et al., A fraction of the mouse genome that is derived from islands of non methylated, CpG-rich DNA, Cell, 1985, 40:91-99.

Ponger Loic et al., "CPGProD: Identifying CpG islands associated with transcription start sites in large genomic mammalian sequences", Bioinformatics (Oxford) 18(4), p. 631-633, Apr. 2002.

Database EMBL (online), "*Mus musculus* ribosomal protein S3 (Rps3) gene, complete cds; and U15a snoRNA and U15b snoRNA genes, complete sequence." EPI assession No. EM: AY043296/ Database assession No. AY043296, Sep. 5, 2001.

Database EMBL (online), "H015I23S HO *Hordeum vulgare* cDNA clone H015I23 5-Prime, mRNA sequence." EBI acession No. EM_PRO:CD057580. Database accession No. CD057580, May 15, 2003.

Dillon, N. & Grosveld, F., "Chromatin domains as potential units of eukaryotic gene function" Curr. Opin. Genet. Dev., 1994, 4, 260-264.

Kioussis, D. & Festenstein, R., "Locus control regions: overcoming heterochromatin-induced gene inactivation in mammals" Curr. Opin. Genet. Dev.,1997, 7, 614-619.

Tazi, J. & Bird, A., "Alternative chromatin structure at CpG islands",Cell 60,1990, 909-920.

Li et al, "Locus control regions: coming of age at a decade plus", Trends in Genetics, 15(10):403-408, Oct. 1999.

Shewchuk and Hardlson, "CpG Islands from the α-Globin Gene Cluster Increase Gene Expression in an Integration-Dependend Manner," Molecular and Cellular Biology, Oct. 1997, 17.

Pikaart, Michael J., "Loss of transcriptional activity of a transgene is accompanied by DNA methylation and histone deacetylation and is prevented by insulators," Genes and Development, 1998, 12:2852-2862.

International Search Report, WO 2006/123097, Oct. 30, 2006 ISA/ EP.

Ortiz, B.D. et al., "Adjacent DNA elements dominantly restrict the ubiquitous activity of a novel chromatin-opening region to specific tissues," EMBO J., 1997, 16, 5037-5045.

(56) References Cited

OTHER PUBLICATIONS

Hardison, R., "Hemoglobins from Bacteria to Man: Evolution of Different Patterns of Gene Expression," J. of Experimental Biology 201, 1099-1117 (Mar. 1998), Cambridge, UK.

Williams Steve et al., "CpG-island fragments from the HNRPA2B1/CBX3 genoic locus reduce silencing and enhance transgene expression from the hCMV promoter/enhancer in mammalian cells" BMC Biotechnology, Biomed Central Ltd, London GB, 5(1) p. 17, Jun. 3, 2005.

* cited by examiner

Figure 2

```
      BamHI
  1  GGATCC TGGT  ACCTAAAACA  GCTTCACATG  GCTTAAAATA  GGGGACCAAT
     CCTAGG ACCA  TGGATTTTGT  CGAAGTGTAC  CGAATTTTAT  CCCCTGGTTA
 51  GTCTTTTCCA  ATCTAAGTCC  CATTTATAAT  AAAGTCCATG  TTCCATTTTT
     CAGAAAAGGT  TAGATTCAGG  GTAAATATTA  TTTCAGGTAC  AAGGTAAAAA
101  AAAGGACAAT  CCTTTCGGTT  TAAAACCAGG  CACGATTACC  CAAACAACTC
     TTTCCTGTTA  GGAAAGCCAA  ATTTTGGTCC  GTGCTAATGG  GTTTGTTGAG
151  ACAACGGTAA  AGCACTGTGA  ATCTTCTCTG  TTCTGCAATC  CCAACTTGGT
     TGTTGCCATT  TCGTGACACT  TAGAAGAGAC  AAGACGTTAG  GGTTGAACCA
201  TTCTGCTCAG  AAACCCTCCC  TCTTTCCAAT  CGGTAATTAA  ATAACAAAAG
     AAGACGAGTC  TTTGGGAGGG  AGAAAGGTTA  GCCATTAATT  TATTGTTTTC
251  GAAAAAACTT  AAGATGCTTC  AACCCCGTTT  CGTGACACTT  TGAAAAAAGA
     CTTTTTTGAA  TTCTACGAAG  TTGGGGCAAA  GCACTGTGAA  ACTTTTTTCT
301  ATCACCTCTT  GCAAACACCC  GCTCCCGACC  CCCGCCGCTG  AAGCCCGGCG
     TAGTGGAGAA  CGTTTGTGGG  CGAGGGCTGG  GGGCGGCGAC  TTCGGGCCGC
351  TCCAGAGGCC  TAAGCGCGGG  TGCCCGCCCC  CACCCGGGAG  CGCGGGCCTC
     AGGTCTCCGG  ATTCGCGCCC  ACGGGCGGGG  GTGGGCCCTC  GCGCCCGGAG
401  GTGGTCAGCG  CATCCGCGGG  GAGAAACAAA  GGCCGCGGCA  CGGGGGCTCA
     CACCAGTCGC  GTAGGCGCCC  CTCTTTGTTT  CCGGCGCCGT  GCCCCGAGT
451  AGGGCACTGC  GCCACACCGC  ACGCGCCTAC  CCCCGCGCGG  CCACGTTAAC
     TCCCGTGACG  CGGTGTGGCG  TGCGCGGATG  GGGGCGCGCC  GGTGCAATTG
501  TGGCGGTCGC  CGCAGCCTCG  GGACAGCCGG  CCGCGCGCCG  CCAGGCTCGC
     ACCGCCAGCG  GCGTCGGAGC  CCTGTCGGCC  GGCGCGCGGC  GGTCCGAGCG
551  GGACGCGGGA  CCACGCGCCG  CCCTCCGGGA  GGCCCAAGTC  TCGACCCAGC
     CCTGCGCCCT  GGTGCGCGGC  GGGAGGCCCT  CCGGGTTCAG  AGCTGGGTCG
601  CCCGCGTGGC  GCTGGGGGAG  GGGGCGCCTC  CGCCGGAACG  CGGGTGGGGG
     GGGCGCACCG  CGACCCCCTC  CCCCGCGGAG  GCGGCCTTGC  GCCCACCCCC
651  AGGGGAGGGG  GAAATGCGCT  TTGTCTCGAA  ATGGGCAAC   CGTCGCCACA
     TCCCCTCCCC  CTTTACGCGA  AACAGAGCTT  TACCCCGTTG  GCAGCGGTGT
701  GCTCCCTACC  CCCTCGAGGG  CAGAGCAGTC  CCCCACTAA   CTACCGGGCT
     CGAGGGATGG  GGGAGCTCCC  GTCTCGTCAG  GGGGTGATT   GATGGCCCGA
751  GGCCGCGCGC  CAGGCCAGCC  GCGAGGCCAC  CGCCCGACCC  TCCACTCCTT
     CCGGCGCGCG  GTCCGGTCGG  CGCTCCGGTG  GCGGGCTGGG  AGGTGAGGAA
801  CCCGCAGCTC  CCGGCGCGGG  GTCCGGCGAG  AAGGGGAGGG  GAGGGGAGCG
     GGGCGTCGAG  GGCCGCGCCC  CAGGCCGCTC  TTCCCCTCCC  CTCCCCTCGC
851  GAGAACCGGG  CCCCCGGGAC  GCGTGTGGCA  TCTGAAGCAC  CACCAGCGAG
     CTCTTGGCCC  GGGGGCCCTG  CGCACACCGT  AGACTTCGTG  GTGGTCGCTC
901  CGAGAGCTAG  AGAGAAGGAA  AGCCACCGAC  TTCACCGCCT  CCGAGCTGCT
     GCTCTCGATC  TCTCTTCCTT  TCGGTGGCTG  AAGTGGCGGA  GGCTCGACGA
```

Figure 2 (cont.)

```
                                       Esp3I
 951  CCGGGTCGCG GGTCTGCAGC GTCTCCGGCC CTCCGCGCCT ACAGCTCAAG
      GGCCCAGCGC CCAGACGTCG CAGAGGCCGG GAGGCGCGGA TGTCGAGTTC
1001  CCACATCCGA AGGGGGAGGG AGCCGGGAGC TGCGCGCGGG GCCGCCGGGG
      GGTGTAGGCT TCCCCCTCCC TCGGCCCTCG ACGCGCGCCC CGGCGGCCCC
1051  GGAGGGGTGG CACCGCCCAC GCCGGGCGGC CACGAAGGGC GGGGCAGCGG
      CCTCCCCACC GTGGCGGGTG CGGCCCGCCG GTGCTTCCCG CCCCGTCGCC
1101  GCGCGCGCGC GGCGGGGGGA GGGGCCGGCG CCGCGCCCGC TGGGAATTGG
      CGCGCGCGCG CCGCCCCCCT CCCCGGCCGC GGCGCGGGCG ACCCTTAACC
1151  GGCCCTAGGG GGAGGGCGGA GGCGCCGACG ACCGCGGCAC TTACCGTTCG
      CCGGGATCCC CCTCCCGCCT CCGCGGCTGC TGGCGCCGTG AATGGCAAGC
1201  CGGCGTGGCG CCCGGTGGTC CCCAAGGGGA GGGAAGGGGG AGGCGGGGCG
      GCCGCACCGC GGGCCACCAG GGGTTCCCCT CCCTTCCCCC TCCGCCCCGC
1251  AGGACAGTGA CCGGAGTCTC CTCAGCGGTG GCTTTTCTGC TTGGCAGCCT
      TCCTGTCACT GGCCTCAGAG GAGTCGCCAC CGAAAAGACG AACCGTCGGA
1301  CAGCGGCTGG CGCCAAAACC GGACTCCGCC CACTTCCTCG CCCGCCGGTG
      GTCGCCGACC GCGGTTTTGG CCTGAGGCGG GTGAAGGAGC GGGCGGCCAC
1351  CGAGGGTGTG GAATCCTCCA GACGCTGGGG GAGGGGGAGT TGGGAGCTTA
      GCTCCCACAC CTTAGGAGGT CTGCGACCCC CTCCCCCTCA ACCCTCGAAT
1401  AAAACTAGTA CCCCTTTGGG ACCACTTTCA GCAGCGAACT CTCCTGTACA
      TTTTGATCAT GGGGAAACCC TGGTGAAAGT CGTCGCTTGA GAGGACATGT
1451  CCAGGGGTCA GTTCCACAGA CGCGGGCCAG GGGTGGGTCA TTGCGGCGTG
      GGTCCCCAGT CAAGGTGTCT GCGCCCGGTC CCCACCCAGT AACGCCGCAC
                                           BspEI
1501  AACAATAATT TGACTAGAAG TTGATTCGGG TGTTTCCGGA AGGGGCCGAG
      TTGTTATTAA ACTGATCTTC AACTAAGCCC ACAAAGGCCT TCCCCGGCTC
1551  TCAATCCGCC GAGTTGGGGC ACGGAAAACA AAAAGGGAAG GCTACTAAGA
      AGTTAGGCGG CTCAACCCCG TGCCTTTTGT TTTTCCCTTC CGATGATTCT
1601  TTTTTCTGGC GGGGGTTATC ATTGGCGTAA CTGCAGGGAC CACCTCCCGG
      AAAAAGACCG CCCCCAATAG TAACCGCATT GACGTCCCTG GTGGAGGGCC
1651  GTTGAGGGGG CTGGATCTCC AGGCTGCGGA TTAAGCCCCT CCCGTCGGCG
      CAACTCCCCC GACCTAGAGG TCCGACGCCT AATTCGGGGA GGGCAGCCGC
1701  TTAATTTCAA ACTGCGCGAC GTTTCTCACC TGCCTTCGCC AAGGCAGGGG
      AATTAAAGTT TGACGCGCTG CAAAGAGTGG ACGGAAGCGG TTCCGTCCCC
1751  CCGGGACCCT ATTCCAAGAG GTAGTAACTA GCAGGACTCT AGCCTTCCGC
      GGCCCTGGGA TAAGGTTCTC CATCATTGAT CGTCCTGAGA TCGGAAGGCG
1801  AATTCATTGA GCGCATTTAC GGAAGTAACG TCGGGTACTG TCTCTGGCCG
      TTAAGTAACT CGCGTAAATG CCTTCATTGC AGCCCATGAC AGAGACCGGC
1851  CAAGGGTGGG AGGAGTACGC ATTTGGCGTA AGGTGGGGCG TAGAGCCTTC
      GTTCCCACCC TCCTCATGCG TAAACCGCAT TCCACCCCGC ATCTCGGAAG
1901  CCGCCATTGG CGGCGGATAG GGCGTTTACG CGACGGCCTG ACGTAGCGGA
      GGCGGTAACC GCCGCCTATC CCGCAAATGC GCTGCCGGAC TGCATCGCCT
```

Figure 2 (cont.)

```
1951 AGACGCGTTA GTGGGGGGGA AGGTTCTAGA AAAGCGGCGG CAGCGGCTCT
     TCTGCGCAAT CACCCCCCCT TCCAAGATCT TTTCGCCGCC GTCGCCGAGA
2001 AGCGGCAGTA GCAGCAGCGC CGGGTCCCGT GCGGAGGTGC TCCTCGCAGA
     TCGCCGTCAT CGTCGTCGCG GCCCAGGGCA CGCCTCCACG AGGAGCGTCT
2051 GTTGTTTCTC GAGCAGCGGC AGTTCTCACT ACAGCGCCAG GACGAGTCCG
     CAACAAAGAG CTCGTCGCCG TCAAGAGTGA TGTCGCGGTC CTGCTCAGGC
2101 GTTCGTGTTC GTCCGCGGAG ATCTCTCTCA TCTCGCTCGG CTGCGGGAAA
     CAAGCACAAG CAGGCGCCTC TAGAGAGAGT AGAGCGAGCC GACGCCCTTT
                           Tth111I
2151 TCGGGCTGAA GCGACTGAGT CCGCGATGGA GGTAACGGGT TTGAAATCAA
     AGCCCGACTT CGCTGACTCA GGCGCTACCT CCATTGCCCA AACTTTAGTT
2201 TGAGTTATTG AAAAGGGCAT GGCGAGGCCG TTGGCGCCTC AGTGGAAGTC
     ACTCAATAAC TTTTCCCGTA CCGCTCCGGC AACCGCGGAG TCACCTTCAG
2251 GGCCAGCCGC CTCCGTGGGA GAGAGGCAGG AAATCGGACC AATTCAGTAG
     CCGGTCGGCG GAGGCACCCT CTCTCCGTCC TTTAGCCTGG TTAAGTCATC
2301 CAGTGGGGCT TAAGGTTTAT GAACGGGTC TTGAGCGGAG GCCTGAGCGT
     GTCACCCCGA ATTCCAAATA CTTGCCCCAG AACTCGCCTC CGGACTCGCA
2351 ACAAACAGCT TCCCCACCCT CAGCCTCCCG GCGCCATTTC CCTTCACTGG
     TGTTTGTCGA AGGGGTGGGA GTCGGAGGGC CGCGGTAAAG GGAAGTGACC
2401 GGGTGGGGGA TGGGGAGCTT TCACATGGCG GACGCTGCCC CGCTGGGGTG
     CCCACCCCCT ACCCCTCGAA AGTGTACCGC CTGCGACGGG GCGACCCCAC
2451 AAAGTGGGGC GCGGAGGCGG GAATTCTTAT TCCCTTTCTA AAGCACGCTG
     TTTCACCCCG CGCCTCCGCC CTTAAGAATA AGGGAAAGAT TTCGTGCGAC
                                Esp3I
2501 CTTCGGGGGC CACGGCGTCT CCTCGG
     GAAGCCCCCG GTGCCGCAGA GGAGCC
```

Figure 7
Ad.CMV-Luc-SV40 p(A)
Ad.1.5 kb(F)UCOE-CMV-Luc-SV40 p(A)
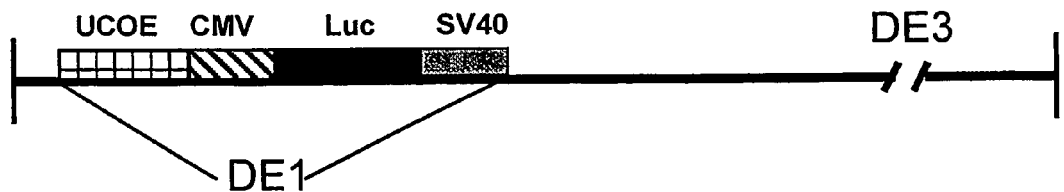

A

Figure 10 (cont.)
B
| CMV | 1.5UCOE-CMV |
DAY 1
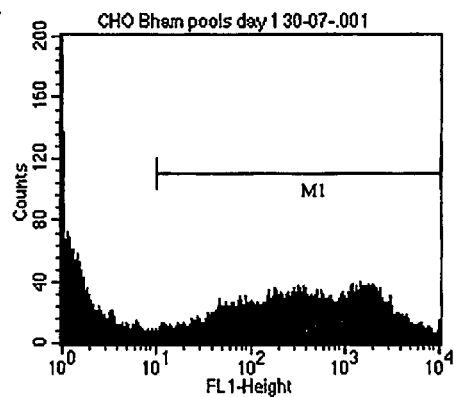 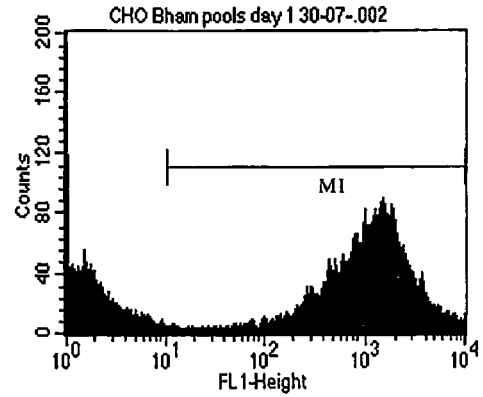
DAY 10
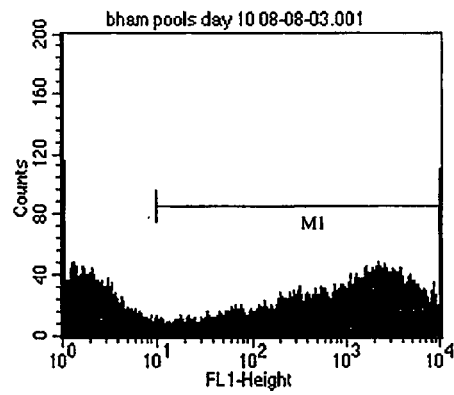 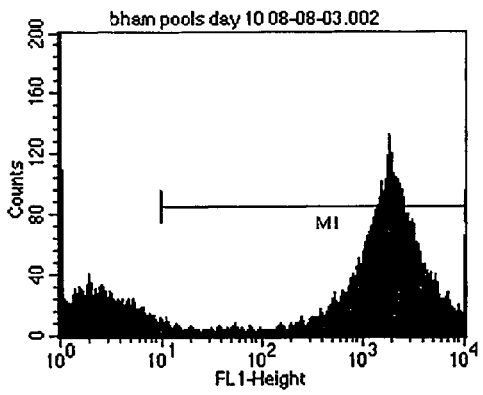
DAY 17
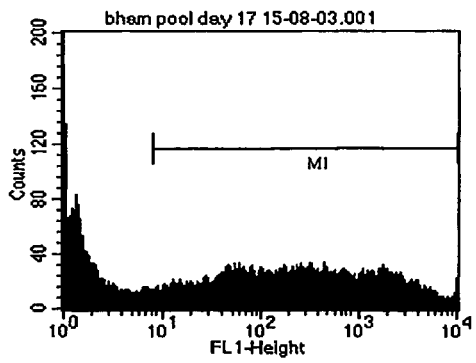 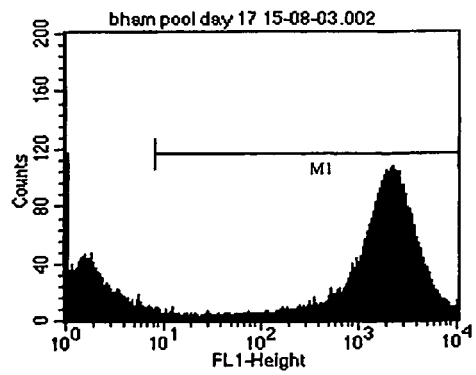

A

B

C

E

SEQUENCE LISTING

```
<160> NUMBER OF SEQ ID NOS: 3

<210> SEQ ID NO 1
<211> LENGTH: 1546
<212> TYPE: DNA
<213> ORGANISM: Homo sapiens

<400> SEQUENCE: 1
ggccctccgc gcctacagct caagccacat ccgaaggggg agggagccgg gagctgcgcg      60
cggggccgcc ggggggaggg gtggcaccgc ccacgccggg cggccacgaa gggcggggca     120
gcgggcgcgc gcgcggcggg gggaggggcc ggcgccgcgc ccgctgggaa ttggggccct     180 aggggggaggg cggaggcgcc gacgaccgcg gcacttaccg ttcgcggcgt ggcgcccggt     240
ggtccccaag gggagggaag gggaggcggg ggcgaggaca gtgaccggag tctcctcagc     300
ggtggctttt ctgcttggca gcctcagcgg ctggcgccaa aaccggactc cgcccacttc     360
ctcgcccgcc ggtgcgaggg tgtggaatcc tccagacgct gggggagggg gagttgggag     420
cttaaaaact agtacccctt tgggaccact ttcagcagcg aactctcctg tacaccaggg     480
gtcagttcca cagacgcggg ccaggggtgg gtcattgcgg cgtgaacaat aatttgacta     540
gaagttgatt cgggtgtttc cggaagggc cgagtcaatc cgccgagttg gggcacggaa      600
aacaaaaagg gaaggctact aagattttc tggcggggt tatcattggc gtaactgcag     660
ggaccacctc ccgggttgag ggggctggat ctccaggctg cggattaagc ccctcccgtc     720
ggcgttaatt tcaaactgcg cgacgtttct cacctgcctt cgccaaggca ggggccggga     780
ccctattcca agaggtagta actagcagga ctctagcctt ccgcaattca ttgagcgcat     840
ttacggaagt aacgtcgggt actgtctctg gccgcaaggg tgggaggagt acgcatttgg     900
cgtaaggtgg ggcgtagagc cttcccgcca ttggcggcgg atagggcgtt tacgcgacgg     960
cctgacgtag cggaagacgc gttagtgggg gggaaggttc tagaaaagcg gcggcagcgg    1020
```

| | |
|---|---|
| ctctagcggc agtagcagca gcgccgggtc ccgtgcggag gtgctcctcg cagagttgtt | 1080 |
| tctcgagcag cggcagttct cactacagcg ccaggacgag tccggttcgt gttcgtccgc | 1140 |
| ggagatctct ctcatctcgc tcggctgcgg gaaatcgggc tgaagcgact gagtccgcga | 1200 |
| tggaggtaac gggtttgaaa tcaatgagtt attgaaaagg gcatggcgag gccgttggcg | 1260 |
| cctcagtgga agtcggccag ccgcctccgt gggagagagg caggaaatcg gaccaattca | 1320 |
| gtagcagtgg ggcttaaggt ttatgaacgg ggtcttgagc ggaggcctga gcgtacaaac | 1380 |
| agcttccccc ccctcagcct cccggcgcca tttcccttca ctggggggtgg gggatgggga | 1440 |
| gctttcacat ggcggacgct gccccgctgg ggtgaaagtg gggcgcggag gcgggaattc | 1500 |
| ttattccctt tctaaagcac gctgcttcgg gggccacggc gtctcc | 1546 |

<210> SEQ ID NO 2
<211> LENGTH: 987
<212> TYPE: DNA
<213> ORGANISM: Homo sapiens

<400> SEQUENCE: 2

| | |
|---|---|
| ccggaagggg ccgagtcaat ccgccgagtt ggggcacgga aaacaaaaag ggaaggctac | 60 |
| taagattttt ctggcggggg ttatcattgg cgtaactgca gggaccacct cccgggttga | 120 |
| gggggctgga tctccaggct gcggattaag cccctcccgt cggcgttaat ttcaaactgc | 180 |
| gcgacgtttc tcacctgcct tcgccaaggc aggggccggg accctattcc aagaggtagt | 240 |
| aactagcagg actctagcct tccgcaattc attgagcgca tttacggaag taacgtcggg | 300 |
| tactgtctct ggccgcaagg gtgggaggag tacgcatttg gcgtaaggtg gggcgtagag | 360 |
| ccttcccgcc attggcggcg datagggcgt ttacgcgacg gcctgacgta gcggaagacg | 420 |
| cgttagtggg gggaaggtt ctagaaaagc ggcggcagcg gctctagcgg cagtagcagc | 480 |
| agcgccgggt cccgtgcgga ggtgctcctc gcagagttgt ttctcgagca gcggcagttc | 540 |
| tcactacagc gccaggacga gtccggttcg tgttcgtccg cggagatctc tctcatctcg | 600 |
| ctcggctgcg ggaaatcggg ctgaagcgac tgagtccgcg atggaggtaa cgggtttgaa | 660 |
| atcaatgagt tattgaaaag gcatggcga ggccgttggc gcctcagtgg aagtcggcca | 720 |
| gccgcctccg tgggagagag gcaggaaatc ggaccaattc agtagcagtg gggcttaagg | 780 |
| tttatgaacg gggtcttgag cggaggcctg agcgtacaaa cagcttcccc accctcagcc | 840 |
| tcccggcgcc atttcccttc actggggggtg ggggatgggg agctttcaca tggcggacgc | 900 |
| tgccccgctg gggtgaaagt ggggcgcgga ggcgggaatt cttattccct ttctaaagca | 960 |
| cgctgcttcg ggggccacgg cgtctcc | 987 |

<210> SEQ ID NO 3
<211> LENGTH: 2526
<212> TYPE: DNA
<213> ORGANISM: Homo Sapiens

<400> SEQUENCE: 3

| | |
|---|---|
| ggatcctggt acctaaaaca gcttcacatg gcttaaaata ggggaccaat gtcttttcca | 60 |
| atctaagtcc catttataat aaagtccatg ttccattttt aaaggacaat cctttcggtt | 120 |
| taaaaccagg cacgattacc caaacaactc acaacggtaa agcactgtga atcttctctg | 180 |
| ttctgcaatc ccaacttggt ttctgctcag aaaccctccc tctttccaat cggtaattaa | 240 |
| ataacaaaag gaaaaaactt aagatgcttc aaccccgttt cgtgacactt tgaaaaagaa | 300 |
| atcacctctt gcaaacaccc gctcccgacc ccgccgctg aagcccggcg tccagaggcc | 360 |

| | | | | |
|---|---|---|---|---|
| taagcgcggg | tgcccgcccc | cacccgggag | cgcgggcctc | gtggtcagcg | catccgcggg | 420 |
| gagaaacaaa | ggccgcggca | cgggggctca | agggcactgc | gccacaccgc | acgcgcctac | 480 |
| ccccgcgcgg | ccacgttaac | tggcggtcgc | cgcagcctcg | ggacagccgg | ccgcgcgccg | 540 |
| ccaggctcgc | ggacgcggga | ccacgcgccg | ccctccggga | ggcccaagtc | tcgacccagc | 600 |
| cccgcgtggc | gctgggggag | ggggcgcctc | cgccggaacg | cgggtggggg | agggggagggg | 660 |
| gaaatgcgct | ttgtctcgaa | atggggcaac | cgtcgccaca | gctccctacc | ccctcgaggg | 720 |
| cagagcagtc | cccccactaa | ctaccgggct | ggccgcgcgc | caggccagcc | gcgaggccac | 780 |
| cgcccgaccc | tccactcctt | cccgcagctc | ccggcgcggg | gtccggcgag | aaggggaggg | 840 |
| gaggggagcg | gagaaccggg | ccccggggac | gcgtgtggca | tctgaagcac | caccagcgag | 900 |
| cgagagctag | agagaaggaa | agccaccgac | ttcaccgcct | ccgagctgct | ccgggtcgcg | 960 |
| ggtctgcagc | gtctccggcc | ctccgcgcct | acagctcaag | ccacatccga | agggggaggg | 1020 |
| agccgggagc | tgcgcgcggg | gccgccgggg | ggaggggtgg | caccgcccac | gccgggcggc | 1080 |
| cacgaagggc | ggggcagcgg | gcgcgcgcgc | ggcgggggga | ggggccggcg | ccgcgcccgc | 1140 |
| tgggaattgg | ggccctaggg | ggagggcgga | ggcgccgacg | accgcggcac | ttaccgttcg | 1200 |
| cggcgtggcg | cccggtggtc | cccaagggga | gggaagggggg | aggcggggcg | aggacagtga | 1260 |
| ccggagtctc | ctcagcggtg | gcttttctgc | ttggcagcct | cagcggctgg | cgccaaaacc | 1320 |
| ggactccgcc | cacttcctcg | cccgccggtg | cgagggtgtg | gaatcctcca | gacgctgggg | 1380 |
| gagggggagt | tgggagctta | aaaactagta | cccctttggg | accactttca | gcagcgaact | 1440 |
| ctcctgtaca | ccaggggtca | gttccacaga | cgcgggccag | gggtgggtca | ttgcggcgtg | 1500 |
| aacaataatt | tgactagaag | ttgattcggg | tgtttccgga | aggggccgag | tcaatccgcc | 1560 |
| gagttggggc | acgaaaaaca | aaaagggaag | gctactaaga | ttttctggc | ggggttatc | 1620 |
| attggcgtaa | ctgcagggac | cacctcccgg | gttgaggggg | ctggatctcc | aggctgcgga | 1680 |
| ttaagcccct | cccgtcggcg | ttaatttcaa | actgcgcgac | gtttctcacc | tgccttcgcc | 1740 |
| aaggcagggg | ccgggaccct | attccaagag | gtagtaacta | gcaggactct | agccttccgc | 1800 |
| aattcattga | gcgcatttac | ggaagtaacg | tcgggtactg | tctctggccg | caagggtggg | 1860 |
| aggagtacgc | atttggcgta | aggtggggcg | tagagccttc | ccgccattgg | cggcggatag | 1920 |
| ggcgtttacg | cgacggcctg | acgtagcgga | agacgcgtta | gtgggggggga | aggttctaga | 1980 |
| aaagcggcgg | cagcggctct | agcggcagta | gcagcagcgc | cgggtcccgt | gcggaggtgc | 2040 |
| tcctcgcaga | gttgtttctc | gagcagcggc | agttctcact | acagcgccag | gacgagtccg | 2100 |
| gttcgtgttc | gtccgcggag | atctctctca | tctcgctcgg | ctgcgggaaa | tcgggctgaa | 2160 |
| gcgactgagt | ccgcgatgga | ggtaacgggt | ttgaaatcaa | tgagttattg | aaaagggcat | 2220 |
| ggcgaggccg | ttggcgcctc | agtggaagtc | ggccagccgc | ctccgtggga | gagaggcagg | 2280 |
| aaatcggacc | aattcagtag | cagtgggggct | taaggtttat | gaacgggtc | ttgagcggag | 2340 |
| gcctgagcgt | acaaacagct | tccccaccct | cagcctcccg | gcgccatttc | ccttcactgg | 2400 |
| gggtggggga | tggggagctt | tcacatggcg | gacgctgccc | cgctggggtg | aaagtggggc | 2460 |
| gcggaggcgg | gaattcttat | tcccttttcta | aagcacgctg | cttcggggc | cacggcgtct | 2520 |
| cctcgg | | | | | 2526 |

EXPRESSION ELEMENTS

FIELD OF THE INVENTION

The present invention relates to a polynucleotide comprising an improved, smaller ubiquitous chromatin-opening element (UCOE). When operably linked to an expressible nucleic acid sequence, this element provides high and reproducible levels of gene expression. The present invention also relates to a vector comprising the polynucleotide sequence, a host cell comprising the vector and use of the polynucleotide, vector or host cell in therapy, or for applications involving protein expression in cell culture.

BACKGROUND OF THE INVENTION

The current model of chromatin structure in higher eukaryotes postulates that genes are organised in "domains" (Dillon, N. & Grosveld, F. Chromatin domains as potential units of eukaryotic gene function. Curr. Opin. Genet. Dev. 4, 260-264 (1994); Higgs, D. R. Do LCRs open chromatin domains? Cell 95, 299-302 (1998)) Chromatin domains are envisaged to exist in either a condensed, "closed", transcriptionally silent state, or in a de-condensed, "open" and transcriptionally competent configuration. The establishment of an open chromatin structure characterised by increased DNaseI sensitivity, DNA hypomethylation and histone hyperacetylation, is considered a pre-requisite to the commencement of gene expression.

The open and closed nature of chromatin regions is reflected in the behaviour of transgenes that are randomly integrated into the host cell genome. Identical constructs give different patterns of tissue-specific and development stage-specific expression when integrated at different locations in the mouse genome (Palmiter, R. D. & Brinster, R. L. *Ann. Ref. Genet.* 20, 465-499 (1986); Allen, N. D. et al. *Nature* 333, 852-855 (1988); Bonnerot, C., Grimber, G., Briand, P. & Nicolas, J. F. *Proc. Natl. Acad. Sci. USA* 87:6331-6335 (1990)).

A variegated expression pattern within a given transgenic mouse tissue, known as position effect variegation (PEV), is also frequently observed (Kioussis, D. & Festenstein, R. *Curr. Opin. Genet. Dev.* 7, 614-619 (1997)). When exogenous genes are integrated into the chromosome of mammalian cells cultures in vitro, many of the integration events result in rapid silencing of the transgene and the remainder give large variability in expression levels (Pikaart, M. J., Recillas-Targa, F. & Felsenfield, G. *Genes Dev.* 12, 2852-2862 (1998); Fussenegger, M., Bailey, J. E., Hauser, H. & Mueller, P. P *Trends Biotech.* 17, 35-42 (1999)). These position effects render transgene expression inefficient, with implication for both basic research and biotechnology applications.

The chromatin domain model of gene organisation suggests that genetic control elements that are able to establish and maintain a transcriptionally competent open chromatin structure should be associated with active regions of the genome.

Locus Control Regions (LCRs) are a class of transcriptional regulatory elements with long-range chromatin remodelling capability. LCRs are functionally defined in transgenic mice by their ability to confer site-of-integration independent, transgene copy number-dependent, physiological levels of expression on a gene linked in cis, especially single copy transgenes Fraser, P. & Grosveld, F. *Curr. Opin. Cell Biol.* 10, 361-365 (1998); Li, Q., Harju, S. & Peterson, K. R. *Trends Genet.* 15: 403-408 (1999). Crucially, such expression is tissue-specific. LCRs are able to obstruct the spread of heterochromatin, prevent PEV (Kioussis, D. & Festenstein, R. *Curr. Opin. Genet. Dev.* 7, 614-619 (1997)) and consist of a series of DNase I hypersensitive (HS) sites which can be located either 5' or 3' of the genes that they regulate (Li, Q., Harju, S. & Peterson, K. R. *Trends Genet.* 15: 403-408 (1999)).

LCRs appear to be comprised of two separate, although not necessarily independent components. First, the establishment of an 'open chromatin domain', and second a dominant transcriptional activation capacity to confer transgene copy number dependent expression (Fraser, P. & Grosveld, F. *Curr. Opin. Cell Biol.* 10, 361-365 (1998). The molecular mechanisms by which LCRs exert their function remain a point of contention (Higgs, D. R. *Cell* 95, 299-302 (1998); Bulger, M. & Groudine, M. *Genes Dev.* 13, 2465-2477 (1999); Grosveld, F. *Curr. Opin. Genet. Dev.* 9 152-157 (1999); Bender, M. A., Bulger, M., Close, J. & Groudine, M. *Mol. Cell* 5, 387-393 (2000).

The generation of cultured mammalian cell lines producing high levels of a therapeutic protein product is a major developing industry. Chromatin position effects make it a difficult, time consuming and expensive process. The most commonly used approach to the production of such mammalian "cell factories" relies on gene amplification induced by a combination of a drug resistance gene (e.g., DHFR, glutamine synthetase (Kaufman R J. *Methods Enzymol* 185, 537-566 (1990)). and the maintenance of stringent selective pressure. The use of vectors containing LCRs from highly expressed gene domains, using cells derived from the appropriate tissue, greatly simplifies the procedure, giving a large proportion of clonal cell lines showing stable high levels of expression (Needham M, Gooding C, Hudson K, Antoniou M, Grosfeld F and Hollis M. *Nucleic Acids Res* 20, 997-1003 (1992); Needham M, Egerton M, Millest A, Evans S, Popplewell M, Cerillo G, McPheat J, Monk A, Jack A, Johnstone D and Hollis M. *Protein Expr Purif* 6, 124-131 (1995).

However, the tissue-specificity of LCRs, although useful in some circumstances, is also a major limitation for many applications, for instance where no LCR is known for the tissue in which expression is required, or where expression in many, or all, tissues is required.

Our co-pending patent applications PCT/GB99/02357 (WO 00/05393), U.S. Ser. No. 09/358,082, GB 0022995.5 and U.S. 60/252,048 incorporated by reference herein, describe elements that are responsible, in their natural chromosomal context, for establishing an open chromatin structure across a locus that consists exclusively of ubiquitously expressed, housekeeping genes. These elements are not derived from an LCR and comprise extended methylation-free CpG islands. We have used the term Ubiquitous Chromatin Opening Element (UCOE) to describe such elements.

In mammalian DNA, the dinucleotide CpG is recognised by a DNA methyltransferase enzyme that methylates cytosine to 5-methylcytosine. However, 5-methylcytosine is unstable and is converted to thymine. As a result, CpG dinucleotides occur far less frequently than one would expect by chance. Some sections of genomic DNA nevertheless do have a frequency of CpG that is closer to that expected, and these sequences are known as "CpG islands". As used herein a "CpG island" is defined as a sequence of DNA, of at least 200 bp, that has a GC content of at least 50% and an observed/expected CpG content ratio of at least 0.6 (i.e. a CpG dinucleotide content of at least 60% of that which would be expected by chance) (Gardiner-Green M and Frommer M. *J Mol Biol* 196, 261-282 (1987); Rice P, Longden I and Bleasby A *Trends Genet* 16, 276-277 (2000).

Methylation-free CpG islands are well-known in the art (Bird et al (1985) *Cell* 40: 91-99, Tazi and Bird (1990) *Cell* 60: 909-920) and may be defined as CpG islands where a substantial proportion of the cytosine residues are not methylated and which usually extend over the 5' ends of two closely spaced (0.1-3 kb) divergently transcribed genes. These regions of DNA are reported to remain hypomethylated in all tissues throughout development (Wise and Pravtcheva (1999) Genomics 60: 258-271). They are often associated with the 5' ends of ubiquitously expressed genes, as well as an estimated 40% of genes showing a tissue-restricted expression profile (Antequera, F. & Bird, A. *Proc. Natl. Acad. Sci. USA* 90, 1195-11999 (1993); Cross, S. H. & Bird, A. P. *Curr. Opin. Genet. Dev.* 5, 309-314 (1995) and are known to be localised regions of active chromatin (Tazi, J. & Bird, A. *Cell* 60, 909-920 (1990).

An 'extended' methylation-free CpG island is a methylation-free CpG island that extends across a region encompassing more than one transcriptional start site and/or extends for more than 300 bp and preferably more than 500 bp. The borders of the extended methylation-free CpG island are functionally defined through the use of PCR over the region in combination with restriction endonuclease enzymes whose ability to digest (cut) DNA at their recognition sequence is sensitive to the methylation status of any CpG residues that are present. One such enzyme is HpaII, which recognises and digests at the site CCGG, which is commonly found within CpG islands, but only if the central CG residues are not methylated. Therefore, PCR conducted with HpaII-digested DNA and over a region harbouring HpaII sites, does not give an amplification product due to HpaII digestion if the DNA is unmethylated. The PCR will only give an amplified product if the DNA is methylated. Therefore, beyond the methylation-free region HpaII will not digest the DNA a PCR amplified product will be observed thereby defining the boundaries of the "extended methylation-free CpG island".

We have demonstrated (WO 00/05393) that regions spanning methylation-free CpG islands encompassing dual, divergently transcribed promoters from the human TATA binding protein (TBP)/proteosome component-B1 (PSMB1) and heterogeneous nuclear ribonucleoprotein A2/B1 (hnRNPA2)/heterochromatin protein 1Hsγ (HP1$^{Hs\gamma}$) gene loci give reproducible, physiological levels of gene expression and that they are able to prevent a variegated expression pattern and silencing that normally occurs with transgene integration within centromeric heterochromatin.

As used herein, the term "reproducible expression" means that the polynucleotide of the invention will direct expression of the expressible gene at substantially the same level of expression irrespective of its chromatin environment and preferably irrespective of the cell type or tissue type in which the polynucleotide of the invention may be. Those of skill in the art will recognize that substantially the same level of expression of the operably-linked expressible gene is achieved, irrespective of the chromatin environment of the claimed polynucleotide, and preferably irrespective of the cell type, assuming that the cell is capable of active gene expression.

We have shown (WO 00/05393) that methylation-free CpG islands associated with actively transcribing promoters possess the ability to remodel chromatin and are thus thought to be a prime determinant in establishing and maintaining an open domain at housekeeping gene loci.

UCOEs confer an increased proportion of productive gene delivery events with improvements in the level and stability of transgene expression. This has important research and biotechnological applications including the generation of transgenic animals and recombinant protein products in cultured cells. We have shown (WO 00/05393) beneficial effects of UCOEs on expression of the CMV-EGFP reporter construct and with the secreted, pharmaceutically valuable protein erythropoietin. The properties of UCOEs also suggest utility in gene therapy, the effectiveness of which is often limited by a low frequency of productive gene delivery events and an inadequate level and duration of expression (Verma, I. M. & Somia, N. *Nature* 389: 239-242 (1997).

Our aforementioned application PCT/GB99/02357 (WO 00/05393), discloses functional UCOE fragments of approximately 4.0 kb, in particular, the '5.5 RNP' fragment defined by nucleotides 4102 to 8286 of FIG. 21 (as disclosed on p11, lines 6 and 7). The same application discloses a '1.5 kb RNP' fragment (FIGS. 22 and 29, derivation described on p51, lines 1 to 5). However, this fragment is actually a 2165 bp BamHI-Tth111I fragment of the '5.5 RNP' fragment described above, consisting of nucleotides 4102 to 6267 of FIG. 21 of that application.

In a further application (WO 02/24930), we disclose artificially-constructed UCOEs composed of fragments of naturally-occurring CpG islands. The fragments disclosed are larger than those claimed in the current application and it was not, at that time, considered possible to use small fragments individually, rather than as mere components of synthetic or 'hybrid' UCOE constructs.

Given these significant implications and wide ranging applications, there is a desire to further optimise transgene expression levels. There is a need to further optimise the levels of transgene expression, particularly in the fields of in vivo gene therapy and for in vitro production of recombinant proteins.

One particular need is to reduce the size of elements used to enhance gene expression. By so doing, smaller vectors may be produced, or vectors with a greater capacity in terms of the size of insert they may stably contain and express.

STATEMENT OF INVENTION

It is an object of the invention to provide smaller chromatin opening elements to enhance the level and reproducibility of operably linked transgenes.

According to the present invention there are provided polynucleotides comprising small functional fragments of UCOEs. Such polynucleotides comprise methylation-free CpG islands of no more than approximately 2 kb, or fragments of larger such islands, of not more than approximately 2 kb.

Although larger polynucleotides comprising extended methylation free CpG islands are known in the art (see applicants' own previous application WO 00/05393), it has not previously been established whether it is possible to use significantly smaller fragments and still maintain the enhancement in levels and consistency of expression obtained with larger UCOEs/methylation-free CpG islands.

As used herein, the term "operably linked" refers to a relationship of operability between elements in the polynucleotides of the invention. "Operably linked" is a term, well known to those of skill in the art, that describes a functional relationship between cis-acting DNA sequences. The exact structural relationship may or may not be relevant and differs for different types of elements. For a promoter, it implies an essentially adjacent (usually within less than 100 bp) position 5' to the open reading frame that it drives. In the case of extended methylation-free CpG islands, it appears that a regional effect on chromatin structure is responsible for increasing the level and consistency of gene expression. By way of example, the element comprising an extended methylation-free CpG-island is positioned immediately 5' of the promoter controlling transcription of the expressible gene.

However, "operably-linked" embraces the possibility of its being positioned elsewhere, as long as a clear functional effect can be demonstrated.

The present invention provides an isolated polynucleotide comprising
- a) an extended methylation-free CpG island;
- b) an expressible open reading frame, operably linked to said extended methylation-free CpG island;
- c) a promoter, operably-linked to said open reading frame, wherein said promoter is not naturally linked to said CpG island;

characterised in that said CpG island is not more than 2 kb in size and wherein reproducible expression of said open reading frame is obtained in two or tissue types.

Alternatively, the polynucleotide comprises a fragment of the human hnRNP A2 gene of no more than 2 kb, preferably no more than 1.6 kb, comprising a 1546 bp Esp3I restriction fragment, more preferably the sequence of FIG. 2, nucleotides 977 to 2522 (SEQ ID NO: 1), or a functional homologue thereof. Preferably, said fragment is orientated in forward orientation.

By 'functional homologue' is meant a polynucleotide sequence capable of hybridising, under stringent conditions, to the disclosed sequence, and which has similar properties of conferring reproducible expression of operably-linked expressible open reading frames in two or more tissues. Stringent hybridisation/washing conditions are well known in the art. For example, nucleic acid hybrids that are stable after washing in 0.1×SSC, 0.1% SDS at 60° C. It is well known in the art that optimal hybridisation conditions can be calculated if the sequence of the nucleic acid is known. For example, hybridisation conditions can be determined by the GC content of the nucleic acid subject to hybridisation. See Sambrook et al (1989), Molecular Cloning; A Laboratory Approach. A common formula for calculating the stringency conditions required to achieve hybridisation between nucleic acid molecules of a specified homology is:

$$T_m = 81.5° C. + 16.6 \text{ Log } [Na^+] + 0.41[\% \, G+C] - 0.63(\% \text{ formamide})$$

Preferably the polynucleotide of the present invention facilitates reproducible expression of an operably-linked gene non-tissue specifically.

In a further preferred embodiment, the polynucleotide comprises a fragment of the human hnRNP A2 gene of no more than approximately 1 kb, preferably comprising a 987 bp BspE1-Esp3I restriction fragment, more preferably comprising the sequence of FIG. 2, nucleotides 1536 to 2522 (SEQ ID NO: 2).

Preferably the polynucleotide of the present invention comprises one or more naturally-occurring promoters.

Preferably the polynucleotide of the present invention comprises dual or bi-directional promoters that transcribe divergently.

In an alternative embodiment, the polynucleotide of the present invention comprises a fragment of the β-actin CpG island/promoter region, preferably of human origin. More preferably the polynucleotide of the present invention comprises a DNA fragment within the range of 100 bp to 2 kb spanning the human β-actin CpG island/promoter region.

In a further alternative, the polynucleotide of the present invention comprises a fragment of the PDCD2 CpG island/promoter region, preferably of human origin. More preferably the polynucleotide of the present invention comprises a DNA fragment within the range from 100 bp to 2 kb spanning the human PDCD2 CpG island/promoter region.

Preferably the polynucleotide of the present invention comprises a DNA fragment within the range from 100 bp to 1.9 kb spanning the human β-actin CpG island/promoter region and a DNA fragment within the range from 100 bp to 2 kb spanning the human PDCD2 CpG island/promoter region. Preferably said fragments are directly adjacent with their promoters oriented divergently.

In another aspect, the invention provides a vector comprising the polynucleotide of invention as disclosed above. Preferably said vector is an expression vector adapted for eukaryotic gene expression.

Typically said adaptation includes, by example and not by way of limitation, the provision of transcription control sequences (promoter sequences) which mediate cell/tissue specific expression.

Promoter and enhancer are terms well-known in the art and include the following features which are provided by example only, and not by way of limitation. Promoters are 5', cis-acting regulatory sequences directly linked to the initiation of transcription. Promoter elements include so-called TATA box and RNA polymerase initiation selection (RIS) sequences which function to select a site of transcription initiation. These sequences also bind polypeptides which function, inter alia, to facilitate transcription initiation selection by RNA polymerase.

Preferably the promoter is selected from CMV, EF-1α, Rous sarcoma virus (RSV) LTR, or HIV2 LTR or combinations of sequences derived therefrom. More preferably the promoter is a CMV immediate/early promoter. Most preferably it is the mouse CMV immediate/early promoter.

In a preferred embodiment of vector, the CpG island of the invention is situated adjacent and 5' to the operative promoter controlling expression of the expressible open reading frame.

Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to trans acting transcription factors (polypeptides) which have been shown to bind specifically to enhancer elements. The binding/activity of transcription factors is responsive to a number of environmental cues which include, by way of example and not by way of limitation, intermediary metabolites (eg glucose), environmental effectors (eg heat). (See Eukaryotic Transcription Factors, by David S Latchman, Academic Press Ltd, San Diego)

Adaptations also include the provision of selectable markers and autonomous replication sequences which both facilitate the maintenance of said vector in either the eukaryotic cell or prokaryotic host. Vectors which are maintained autonomously are referred to as episomal vectors. Episomal vectors are desirable since they are self-replicating and so persist without the need for integration. Episomal vectors of this type are described in WO98/07876.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well-known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

The vector may be an episomal vector or an integrating vector. Preferably, the vector is a plasmid. Alternatively, the vector may be a virus, such as an adenovirus, adeno-associated virus, a herpesvirus, vaccinia virus, lentivirus or other retrovirus.

Preferably the vector comprises an operably linked gene that is a therapeutic nucleic acid. Such a therapeutic nucleic acid may act by replacing or supplementing the function of a defective gene causing a disease such as cystic fibrosis, thalassaemia, sickle anaemia, Fanconi's anaemia, haemophilia, severe combined immunodeficiency (SCID), phenylketonuria (PKU), alpha-1 antitrypsin deficiency, Duchenne muscular dystrophy, ornithine transcarbamylase deficiency or osteogenesis imperfecta. Alternatively, it may encode a cytotoxic agent or prodrug-converting enzyme selectively expressed in a target cell, such as a malignant cancer cell, in order to kill it. Such applications, and many others, are well-known to those of skill in the art and the relevance of the current invention in enhancing the expression of therapeutic nucleic acids will be clear to such skilled practitioners.

Most preferably the vector comprises any one of SEQ ID Nos 1 or 2, a CMV promoter, a multiple cloning site, a polyadenylation sequence and genes encoding selectable markers under suitable control elements.

Also provided is a host cell transfected with the vector. Preferably this is a eukaryotic cell, more preferably a mammalian cell, most preferably a human or rodent cell.

Alternatively it may be a plant cell.

Another aspect of the invention is the use of any of the isolated polynucleotides, methylation-free extended CpG islands (in particular as disclosed by SEQ ID Nos 1 or 2), vectors or host cells disclosed above in therapy, in particular, their use in gene therapy.

The present invention also provides use of the polynucleotide, vector or host cell in the manufacture of a medicament or composition for use in gene therapy.

The present invention also provides a method of treatment, comprising administering to a patient in need of such treatment an effective dose of the polynucleotide, vector or host cell of the present invention. Preferably the patient is suffering from a disease treatable by gene therapy.

The present invention also provides a pharmaceutical composition comprising the polynucleotide and/or the vector and/or host cell, optionally in admixture with a pharmaceutically acceptable carrier or diluent, for therapy to treat a disease or provide the cells of a particular tissue with an advantageous protein or function.

The polynucleotide, vector or host cell of the invention or the pharmaceutical composition may be administered via a route which includes systemic intramuscular, intravenous, aerosol, oral (solid or liquid form), topical, ocular, rectal, intraperitoneal and/or intrathecal and local direct injection.

The exact dosage regime will, of course, need to be determined by individual clinicians for individual patients and this, in turn, will be controlled by the exact nature of the protein expressed by the gene of interest and the type of tissue that is being targeted for treatment.

The dosage also will depend upon the disease indication and the route of administration. The number of doses will depend upon the disease, and the efficacy data from clinical trials.

The amount of polynucleotide or vector DNA delivered for effective gene therapy according to the invention will preferably be in the range of between 50 ng-1000 µg of vector DNA/kg body weight; and more preferably in the range of between about 1-100 µg vector DNA/kg.

Although it is preferred according to the invention to administer the polynucleotide, vector or host cell to a mammal for in vivo cell uptake, an ex vivo approach may be utilised whereby cells are removed from an animal, transduced with the polynucleotide or vector, and then re-implanted into the animal. The liver, for example, can be accessed by an ex vivo approach by removing hepatocytes from an animal, transducing the hepatocytes in vitro and re-implanting the transduced hepatocytes into the animal (e.g., as described for rabbits by Chowdhury et al., *Science* 254:1802-1805, 1991, or in humans by Wilson, *Hum. Gene Ther.* 3:179-222, 1992). Such methods also may be effective for delivery to various populations of cells in the circulatory or lymphatic systems, such as erythrocytes, T cells, B cells and haematopoietic stem cells.

In a further aspect, the invention provides the use of the polynucleotides vectors or host cells of the invention in a cell culture system in order to obtain a desired gene product. Preferably, the expressible nucleic acid encodes a recombinant protein for expression in an in vitro cell culture system.

Suitable cell culture systems are well known in the art and are fully described in the body of literature known to those skilled in the art. There is provided a method for the production of a polypeptide according to the invention comprising:
  providing a cell transformed/transfected with a polynucleotide according to the invention;
  ii) growing said cell in conditions conducive to the manufacture of said polypeptide; and
  iii) purifying said polypeptide from said cell, or its growth environment.

Alternatively, the expressible gene encodes a non-polypeptide product, such as RNA. Such RNA may be an antisense RNA capable of inhibiting expression of a particular gene at a post-transcriptional level, or may have an enzymatic (ribozyme) or other function, such as a ribosomal RNA.

Also provided is the use of an extended methylation-free CpG island polynucleotide according to either of SEQ ID NOs:1 or 2 to increase the expression of an endogenous gene comprising inserting the polynucleotide into the genome of a cell in a position operably associated with the endogenous gene thereby increasing the level of expression of the gene.

In another embodiment of the invention there is provided a non-human transgenic animal comprising any of the polynucleotides or vectors of the invention or any of the extended methylation-free CpG islands of the invention, wherein said CpG island has been introduced artificially. Methods of making transgenic mice (Gordon et al., *Proc. Natl. Acad. Sci. USA* 77:7380 (1980); Harbers et al., *Nature* 293:540 (1981); Wagner et al., *Proc. Natl. Acad. Sci. USA* 78:5016 (1981); and Wagner et al., *Proc. Natl. Acad. Sci. USA* 78:6376 (1981), sheep pigs, chickens (see Hammer et al., *Nature* 315:680 (1985)), etc., are well-known in the art and are contemplated for use according to the invention.

Such transgenic animals containing the polynucleotide of the invention also may be used for long-term production of a protein of interest.

There is also provided a mammalian model for determining the efficacy of gene therapy using the polynucleotide, vector or host cell of the invention. The mammalian model comprises a transgenic animal whose cells contain the vector of the present invention. Such animals permit testing prior to clinical trials in humans.

The present invention also provides the use of the polynucleotides and extended methylation-free CpG islands of the present invention in producing transgenic plants.

The generation of transgenic plants that have increased yield, or increased resistance to disease, pests, drought or salt are well known to those skilled in the art. The present invention also provides for transgenic plant containing cells that contain the polynucleotide of the present invention. Some or all of the cells comprising the polynucleotide of the invention may originate from plants.

The present invention also relates to the use of polynucleotides, vectors or extended methylation-free CpG islands of the present invention in functional genomics applications. Functional genomics relates principally to the identification of genes specifically expressed in particular cell types or disease states and now provides thousands of novel gene sequences of potential interest for drug discovery or gene therapy purposes. The major problem in using this information for the development of novel therapies lies in how to determine the functions of these genes. The polypeptides of the invention can be used in a number of functional genomic applications in order to determine the function of gene sequences. The functional genomic applications of the present invention include, but are not limited to:

(1) Using polynucleotides of the present invention to achieve sustained expression of anti-sense versions of the gene sequences or ribozyme knockdown libraries, thereby determining the effects of inactivating the gene on cell phenotype.

(2) Using polynucleotides of the present invention to prepare expression libraries for the gene sequences, such that delivery into cells will result in reliable, reproducible, sustained expression of the gene sequences. The resulting cells, expressing the gene sequences can be used in a variety of approaches to function determination and drug discovery. For example, raising neutralizing antibodies to the gene product; rapid purification of the protein product of the gene itself for use in structural, functional or drug screening studies; or in cell-based drug screening.

(3) Using polynucleotides of the present invention in approaches involving mouse embryonic stem (ES) cells and transgenic mice. One of the most powerful functional genomics approaches involves random insertion into genes in mouse ES cells of constructs which only allow drug selection following insertion into expressed genes, and which can readily be rescued for sequencing (G. Hicks et al., Nature Genetics, 16, 338-334). Transgenic mice with knockout mutations in genes with novel sequences can then readily be made to probe their function. At present this technology works well for the 10% of mouse genes which are well expressed in mouse ES cells. Incorporation of the polynucleotides of the present invention into the integrating constructs will enable this technique to be extended to identify all genes expressed in mice.

DETAILED DESCRIPTION OF THE INVENTION

The invention will now be described by way of example only and with reference to the accompanying figures wherein;

FIG. 2 shows the nucleotide sequence of HP-1/hnRNPA2 locus (SEQ ID NO:3) indicating BamHI, Esp3I, BspEI and Tth111I restriction sites.

Figure 3:
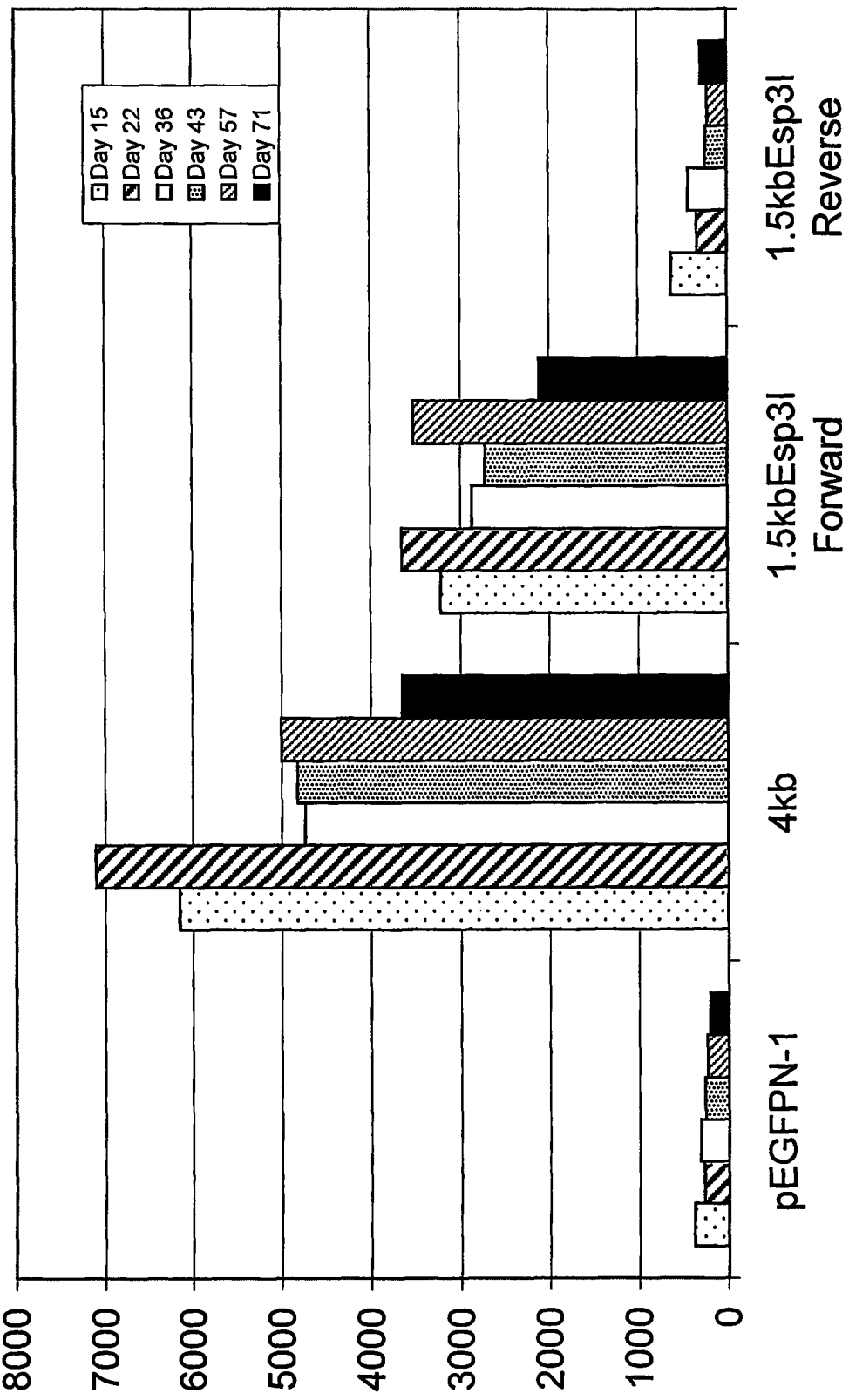

FIG. 3 shows expression of an EGFP reporter gene operably linked to the 4 kb and 1.5 kb (in both orientations) CpG island fragments. FACScan data expressed as median fluorescence over 71 days.

Figure 4:
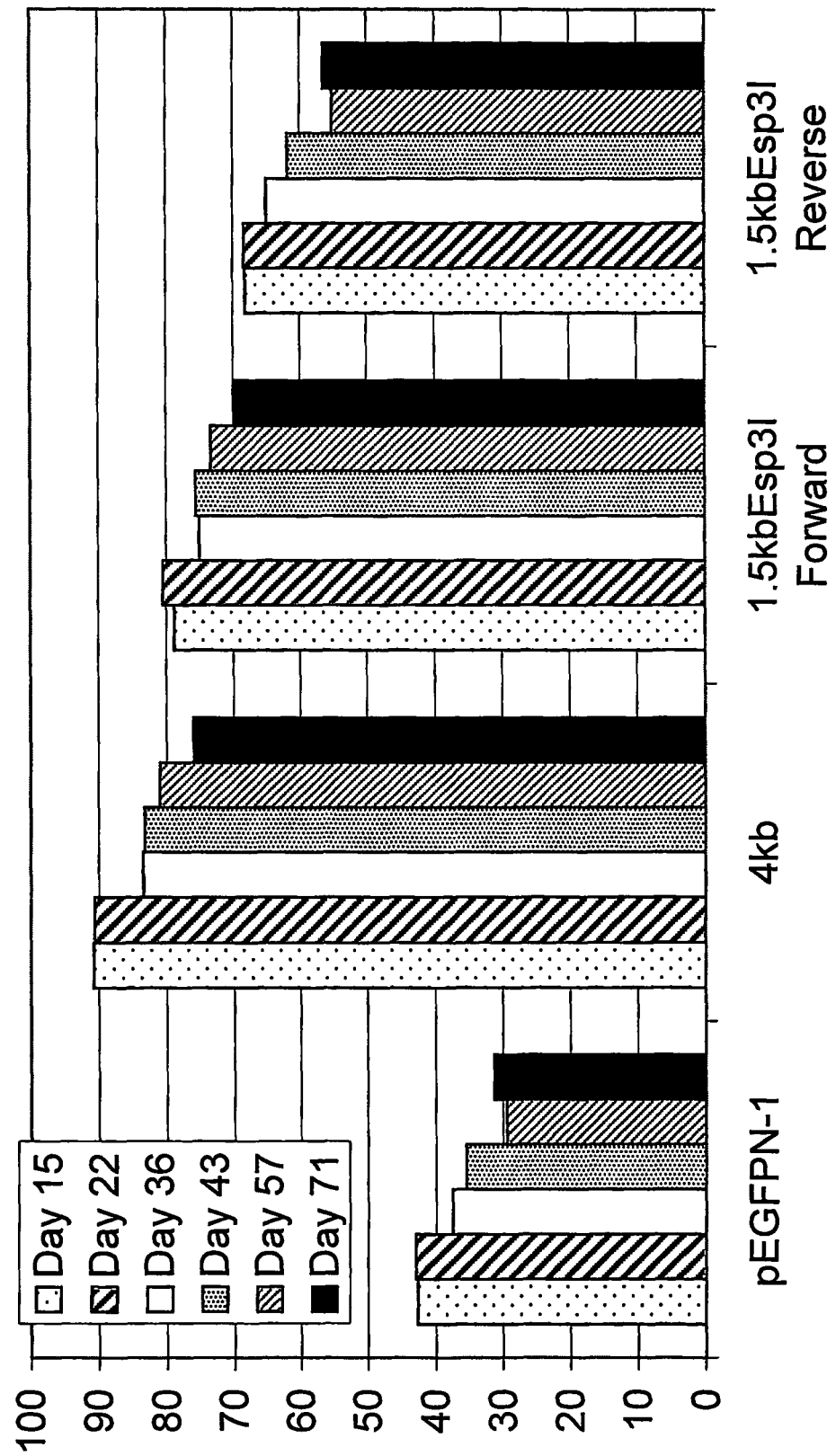

FIG. 4 shows expression of an EGFP reporter gene operably linked to the 4 kb and 1.5 kb (in both orientations) CpG island fragments. FACScan data expressed as % positive cells over 71 days.

Figure 5:
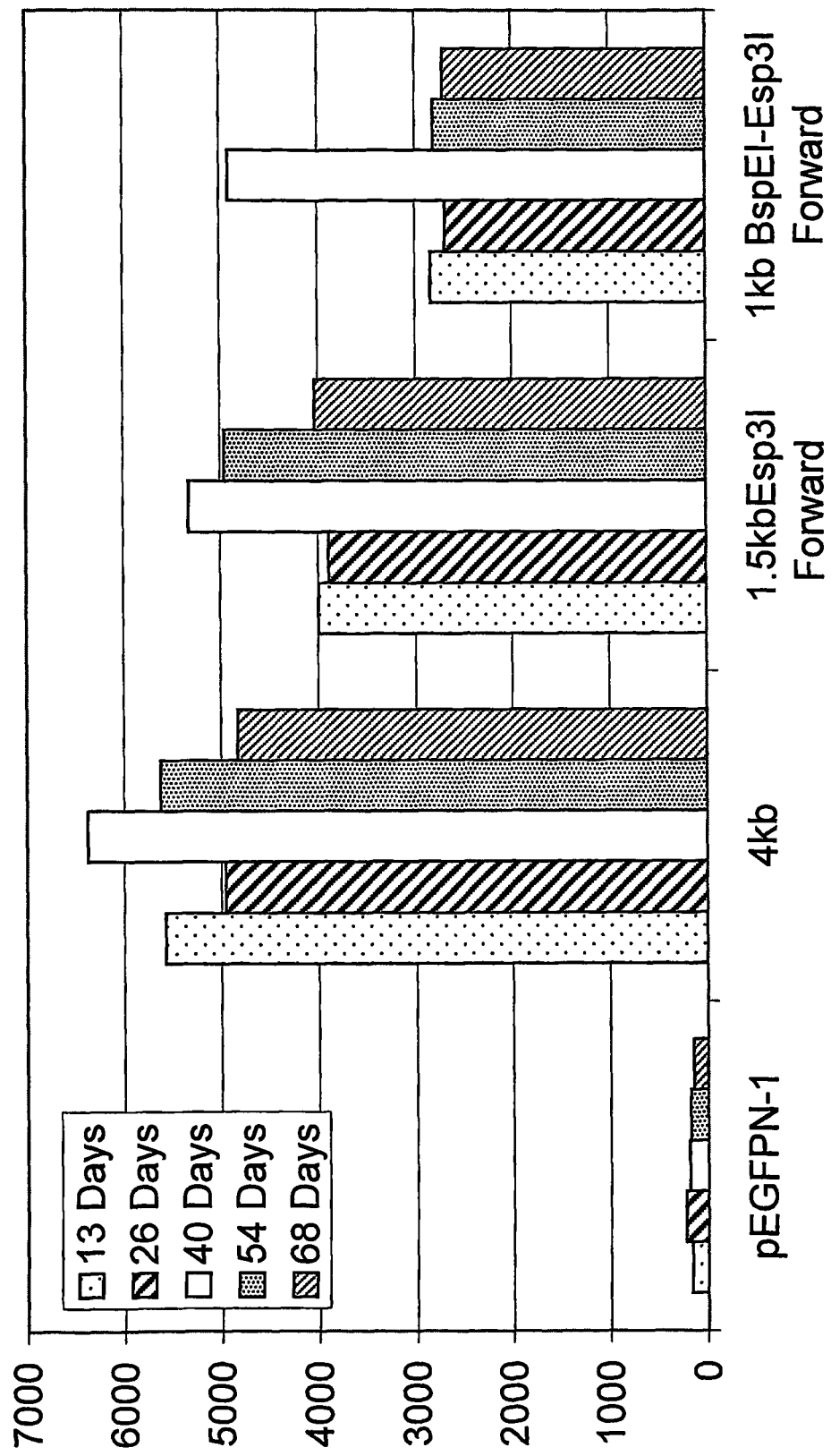
Figure 6:
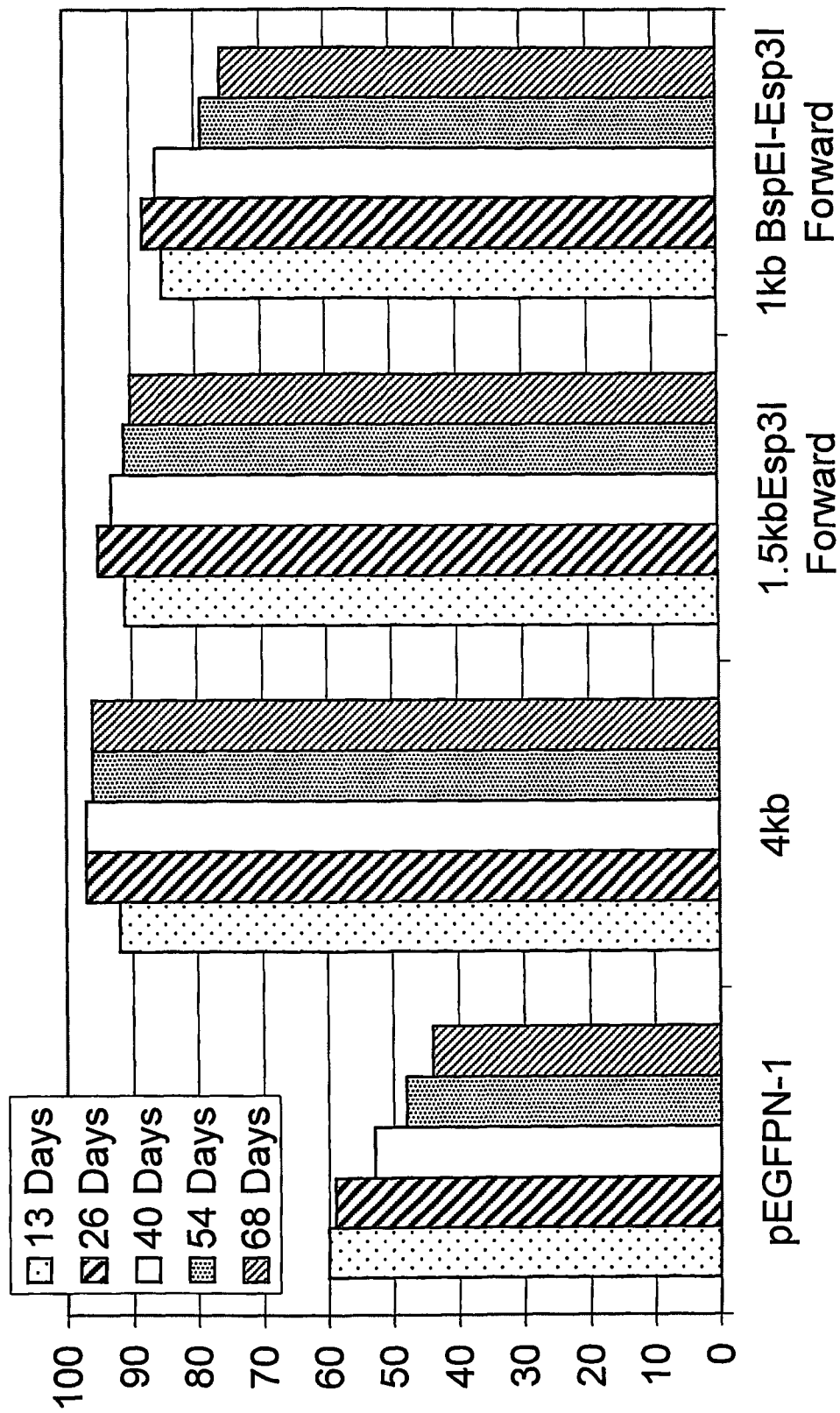

FIG. 5 shows expression of an EGFP reporter gene operably linked to the 4 kb, 1.5 kb and 1 kb CpG island fragments. FACScan data expressed as median fluorescence over 68 days FIG. 6 shows expression of an EGFP reporter gene operably linked to the 4 kb, 1.5 kb and 1 kb CpG island fragments. FACScan data expressed as % positive cells over 68 days FIG. 7 shows the structure of the two adenoviral constructs Ad.CMV-Luc-SV40p(A) and Ad. 1.5 kb(F)UCOE-CMV-Luc-SV40p(A), which are based on Adenovirus serotype 5. The luciferase expression cassettes were inserted into the E1 region in a left to right orientation. The E1 and E3 regions are deleted from the viruses. Due to deletion of E1 the viruses are replication-defective. CMV (cytomegalovirus) is the human CMV enhancer/promoter. SV40p(A) is the SV40 virus late polyadenylation signal from pGL3basic (Promega).

Figure 8:
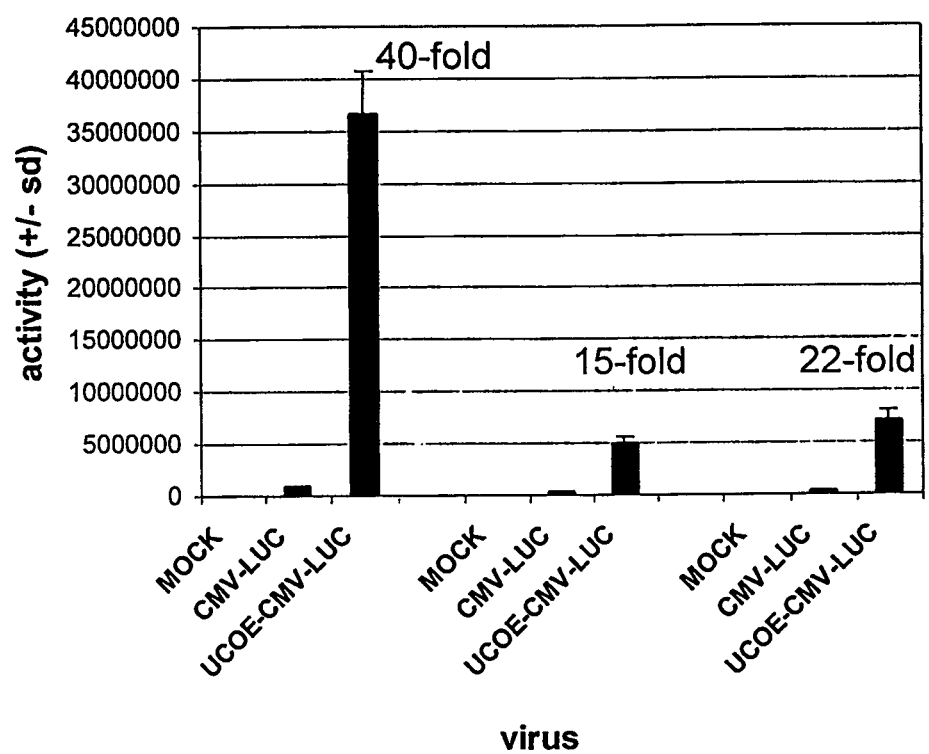

FIG. 8 shows that a 1.5 kb UCOE boosts gene expression in HeLa cells when delivered by means of an adenoviral vector. HeLa cells were infected at an MOI of 50 for 2-3 hours in 200 μl infection medium (normal HeLa medium containing only 1% FCS) with the viruses Ad.CMV-Luc-SV40p(A) and Ad.1.5 kb(F)UCOE-CMV-Luc-SV40p(A). After incubation, 2 ml complete medium was added and cells were seeded into 6-well plates. Luciferase activity was analysed 2 days after infection. Results from three independent experiments are shown. Experiments were done in triplicates. Shown is the mean+/− the standard deviation.

Figure 9:
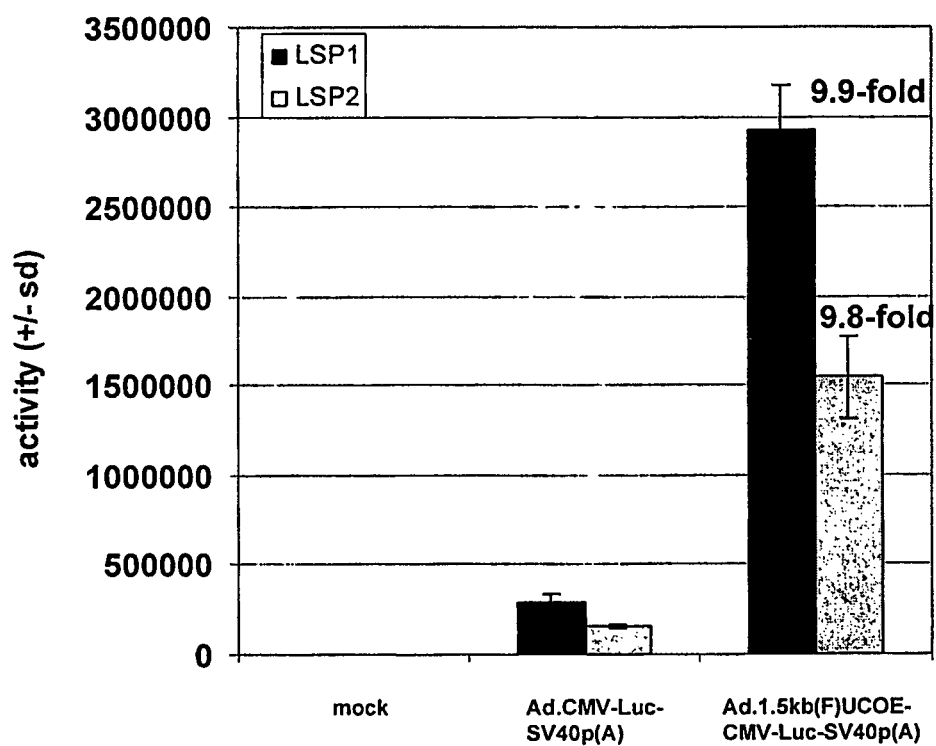

FIG. 9 shows that the 1.5 kb UCOE effect is independent of the viral preparation. HeLa cells were infected at an MOI of 50 for 2-3 hours in 200 μl infection medium (normal Hela medium containing only 1% FCS) with the viruses Ad.CMV-Luc-SV40p(A) and Ad.1.5 kb(F)UCOE-CMV-Luc-SV40p(A) from two independent viral preparations, each. After incubation, 2 ml complete medium was added and cells were seeded into 6-well plates. Luciferase activity was analysed 2 days after infection. Results from one representative experiment is shown. Experiments were done in triplicates.

Figure 10:
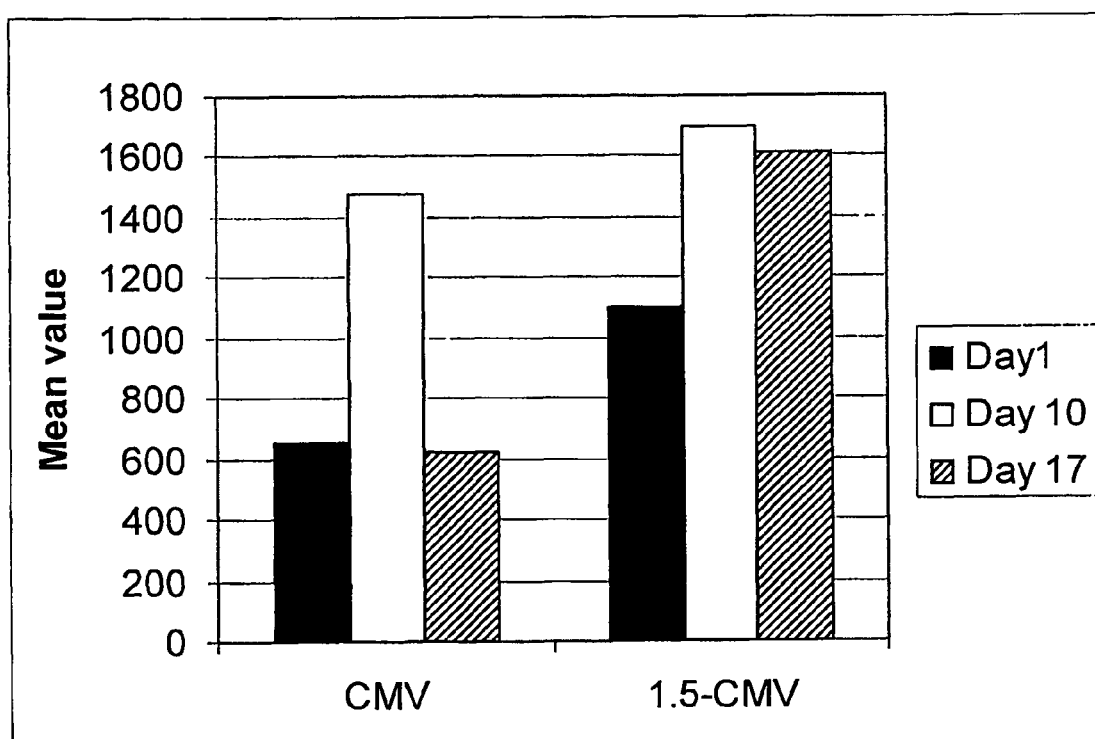

FIG. 10 shows that the 1.5 kb UCOE increases transgene expression level and stability in retrovirally transduced CHO-K1 pools. (A) Mean GFP values over time for FACS-Sorted CHO-K1 pools (36,000 cells originally FACS-sorted) after retroviral transduction for CMV and 1.5UCOE-CMV constructs. Day1 refers to the $1^{st}$ day of measurement (8 days after FACS-Sorting). (B) Histograms of the FACS-sorted CHO-K1 pools for each time point of measurement.

Figure 11:
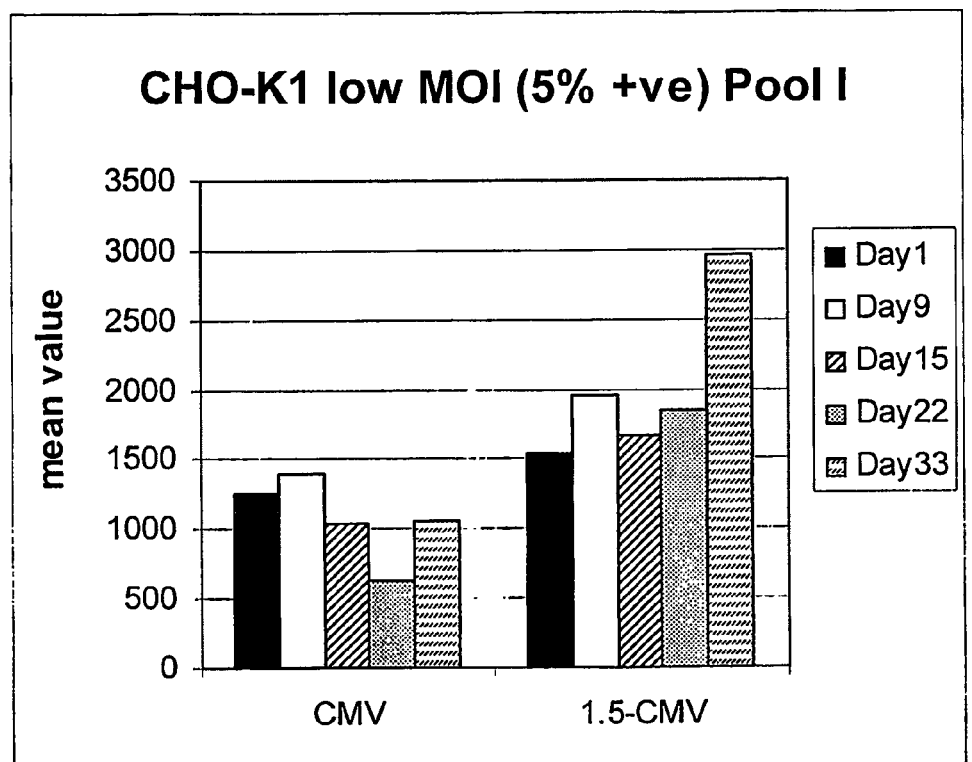
Figure 11:
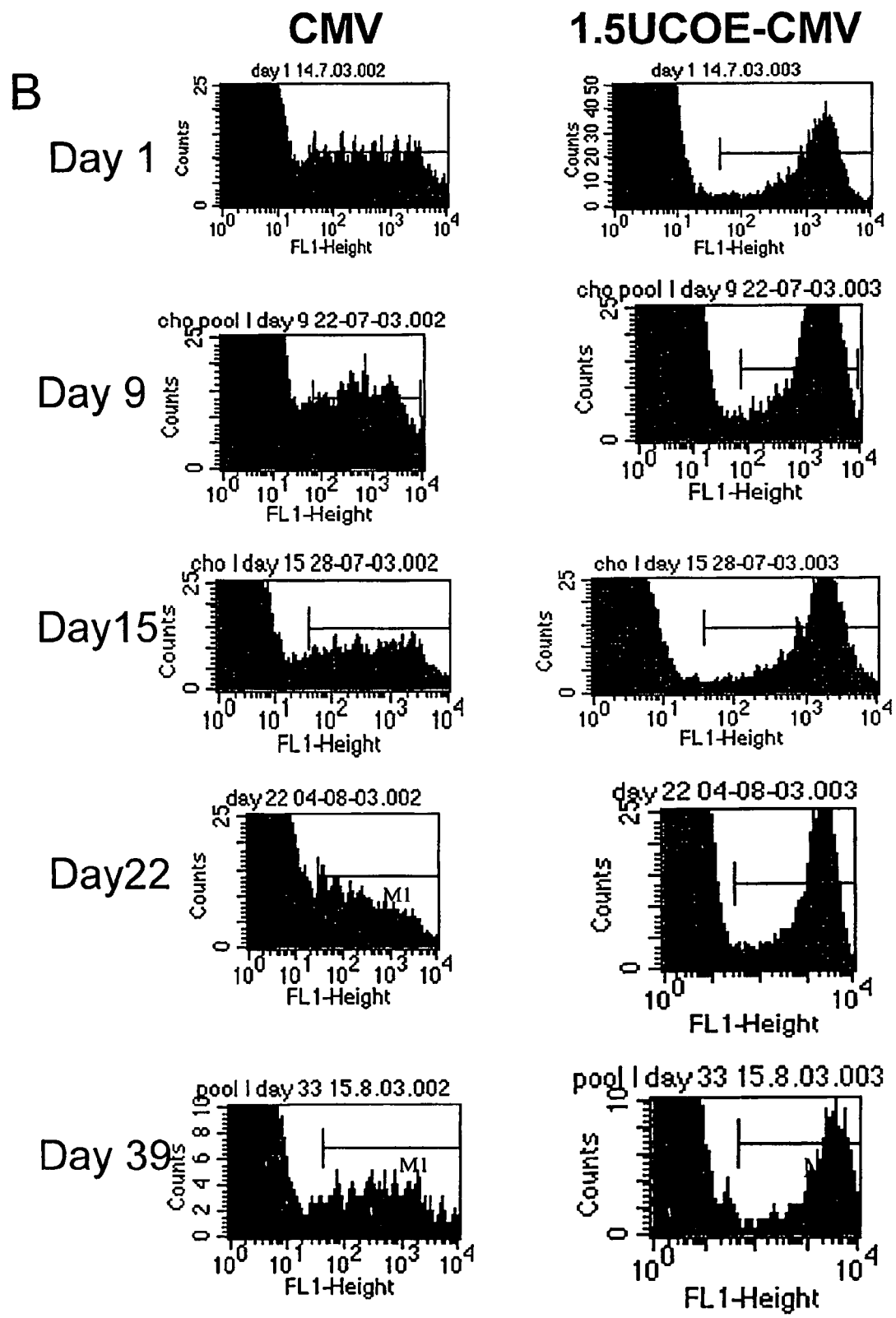

FIG. 11 shows GFP expression of transduced CHO-K1 (pool I) after low MOI infection. (A) Mean GFP values for GFP positive (M1) CHO-K1 populations after retroviral transduction for each time point. The CMV population started with 3.19% GFP-positive cells and the 1.5UCOE-CMV population with 4.99% GFP-positive cells. (B) Histograms for the populations at each time point.

Figure 12:
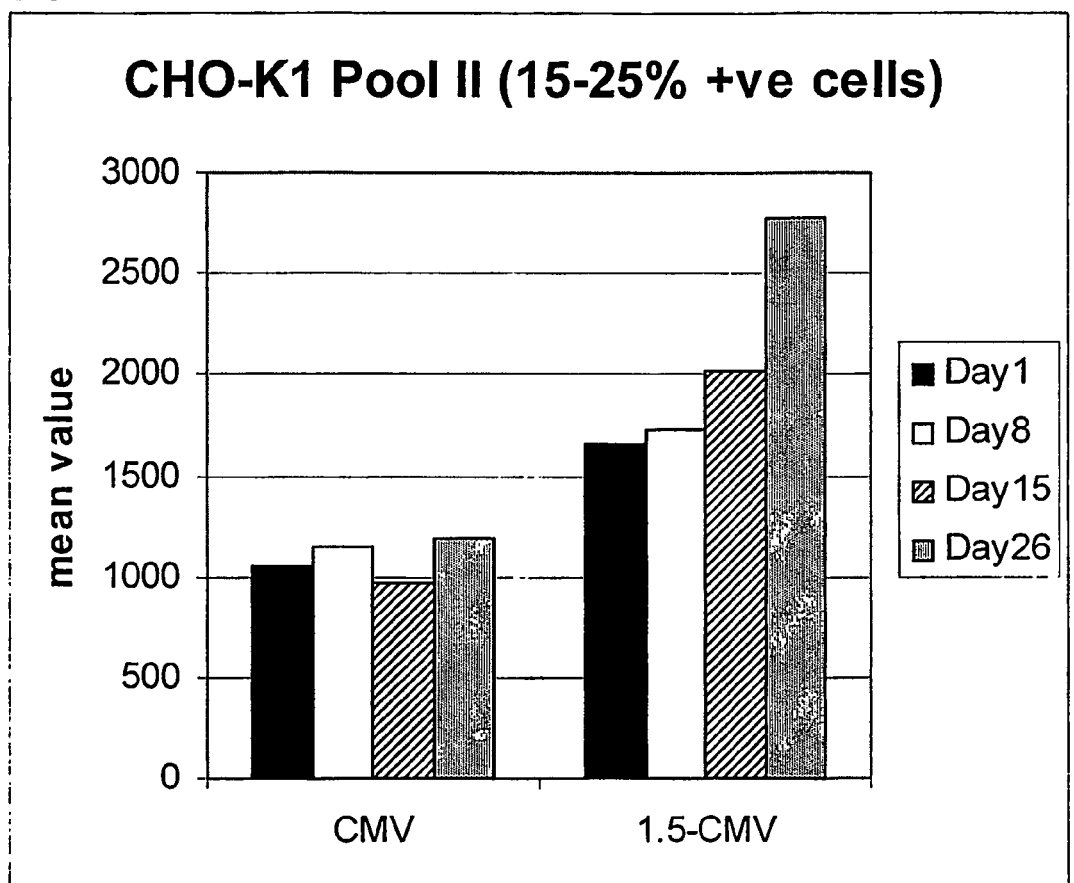
Figure 12:
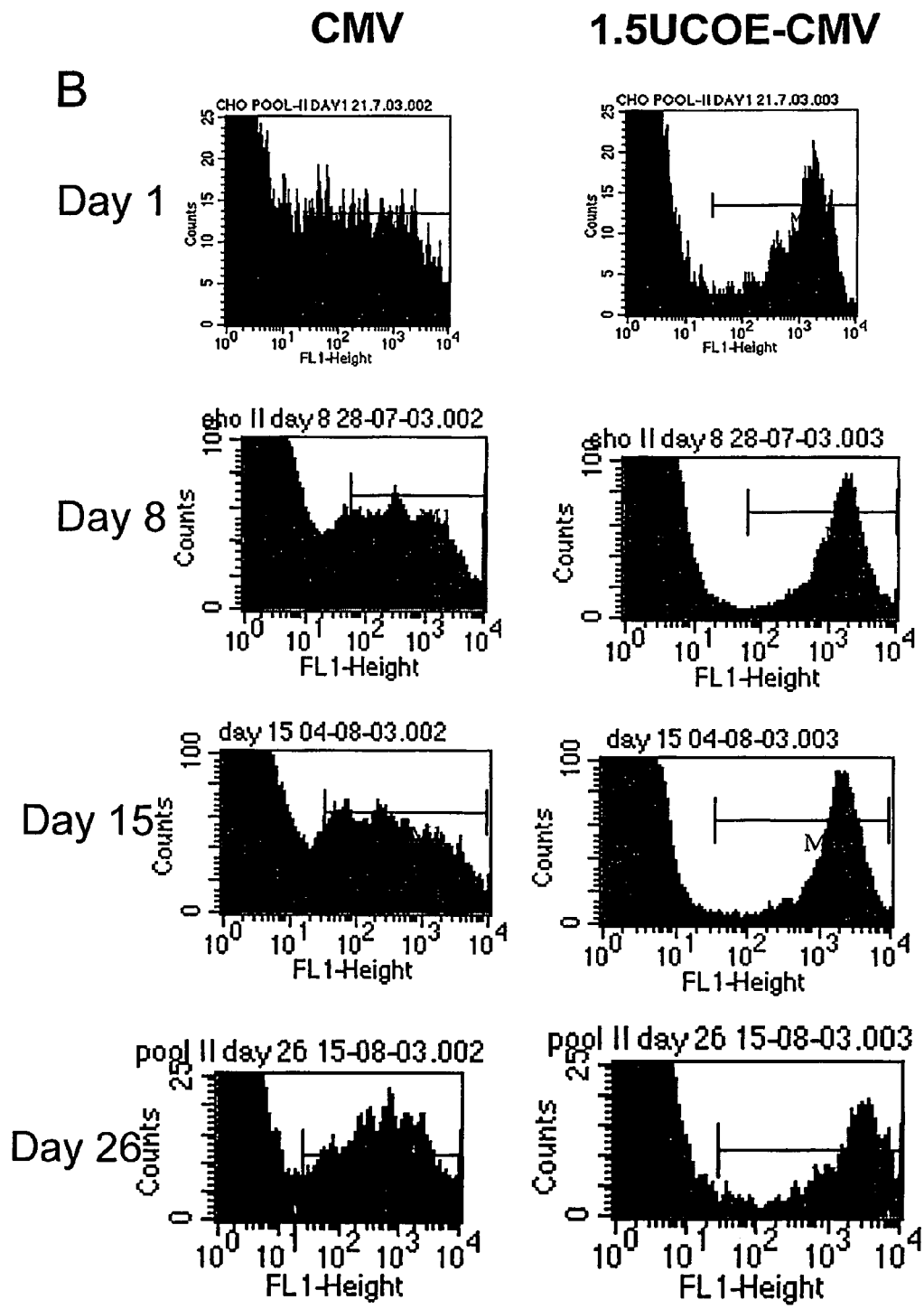

FIG. 12 shows GFP expression of transduced CHO-K1 (pool II) after intermediate MOI infection. (A) Mean GFP values for GFP positive (M1) CHO-K1 populations after retroviral transduction for each time point. The CMV population started with 25.2% GFP-positive cells and the 1.5UCOE-CMV population with 14.35% GFP-positive cells. (B) Histograms of the populations for each time point.

Figure 13:
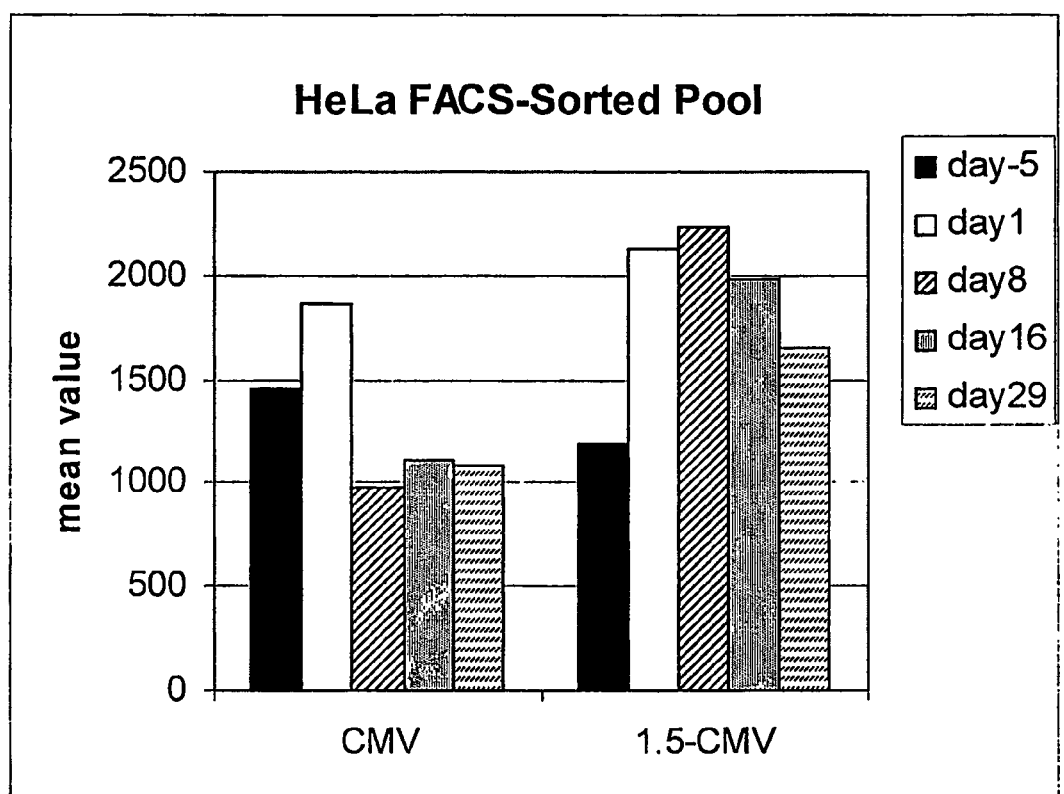
Figure 13:
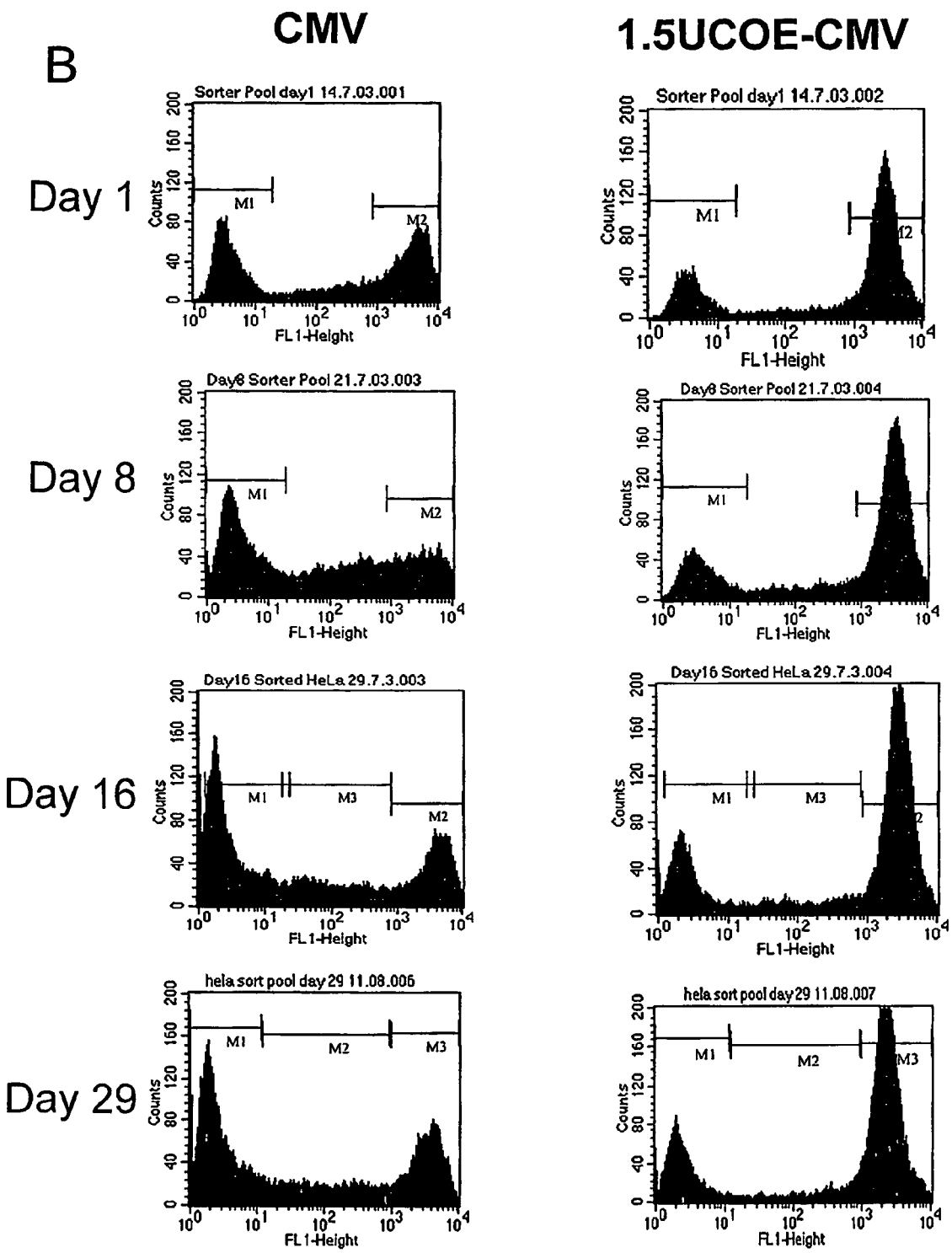

FIG. 13 shows that the 1.5 kb UCOE increases transgene expression level and stability in retrovirally transduced HeLa pools. (A) Mean GFP values over time for FACS-sorted HeLa pools (10,000 cells originally FACS-sorted) after retroviral transduction for CMV and 1.5UCOE-CMV constructs. Day1 refers to the 1$^{st}$ day of measurement (5 days after FACS-sorting). (B) Histograms of the FACS-sorted HeLa pools for each time point of measurement.

Figure 14:
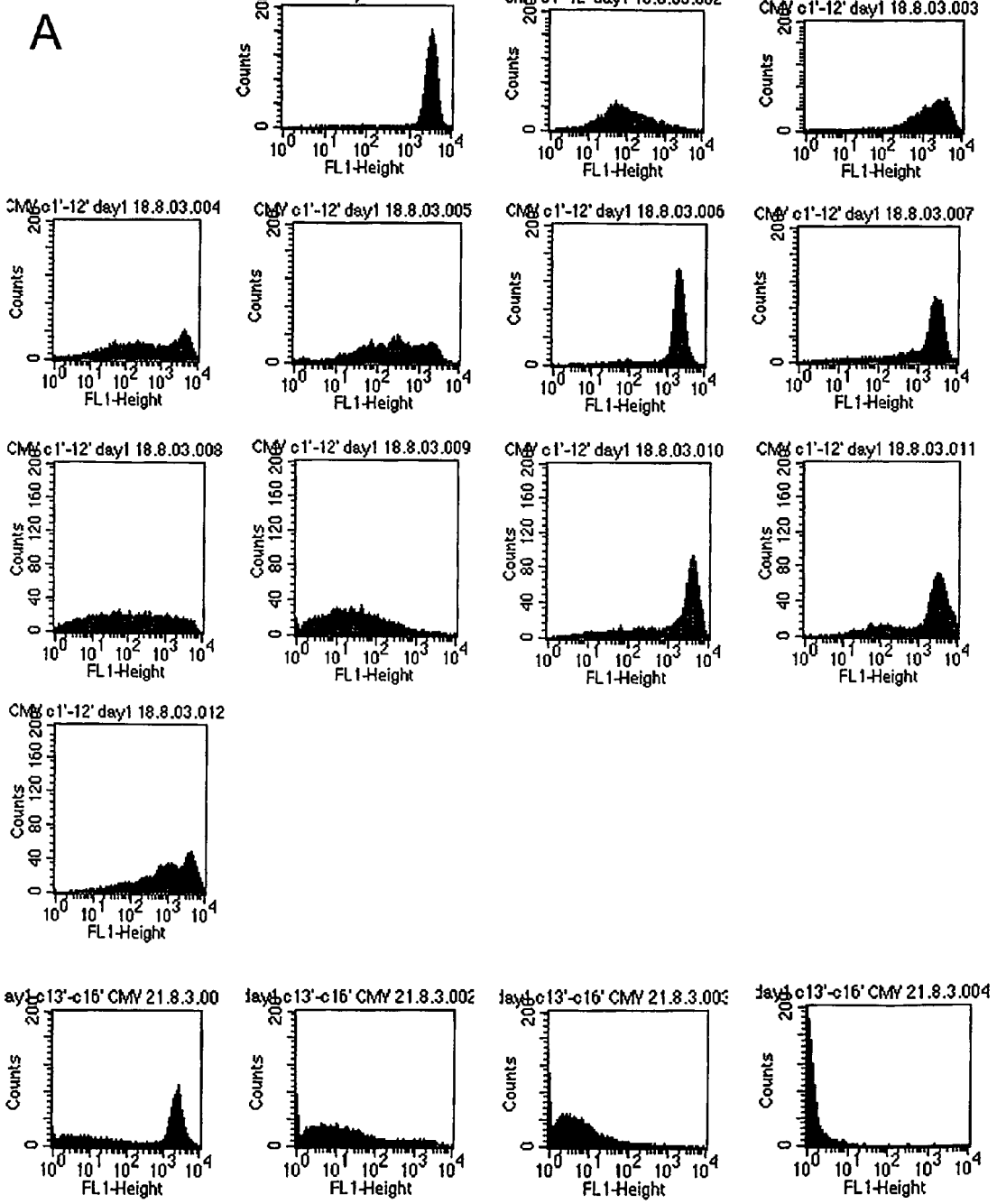
Figure 14:
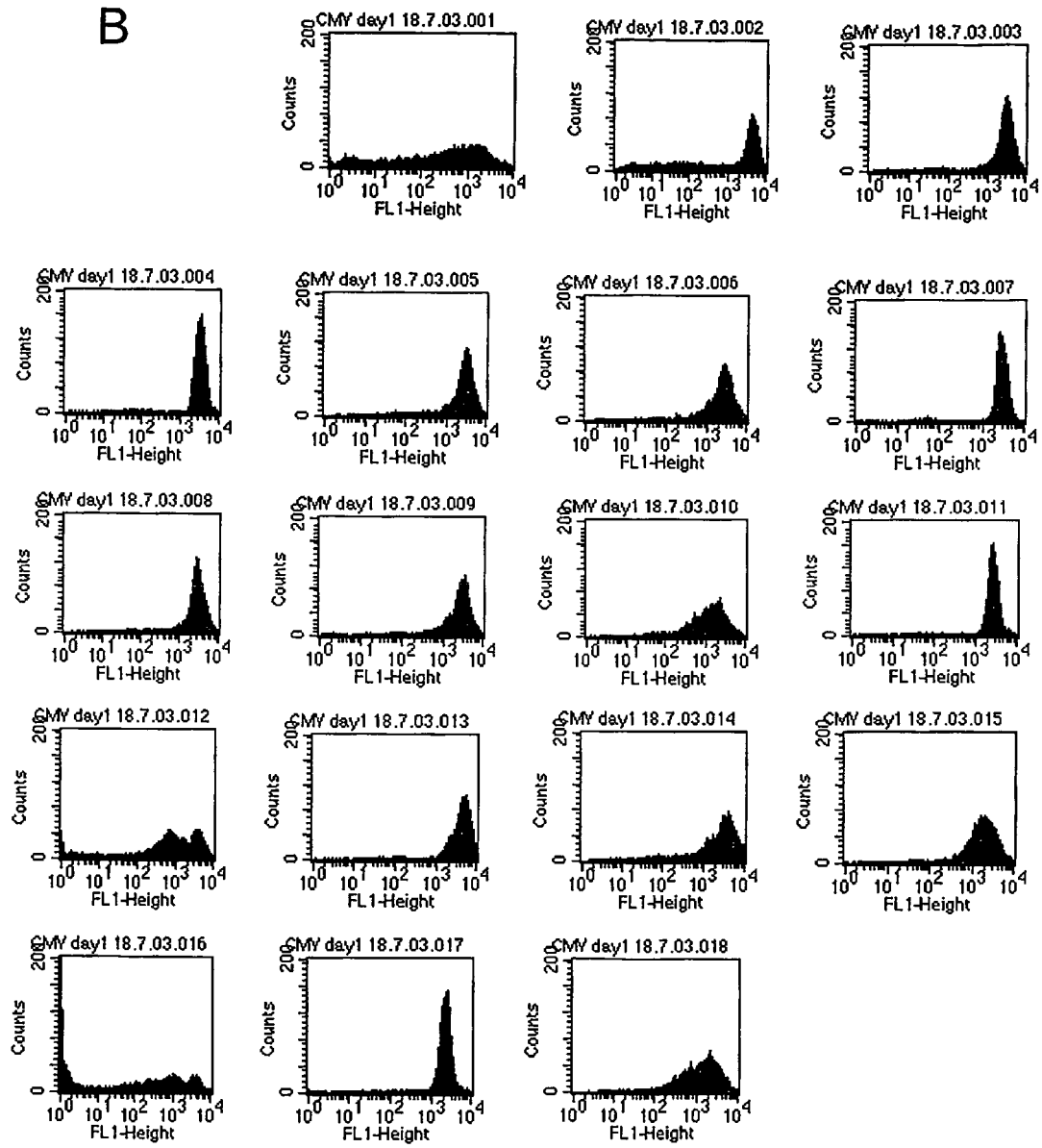
Figure 14:
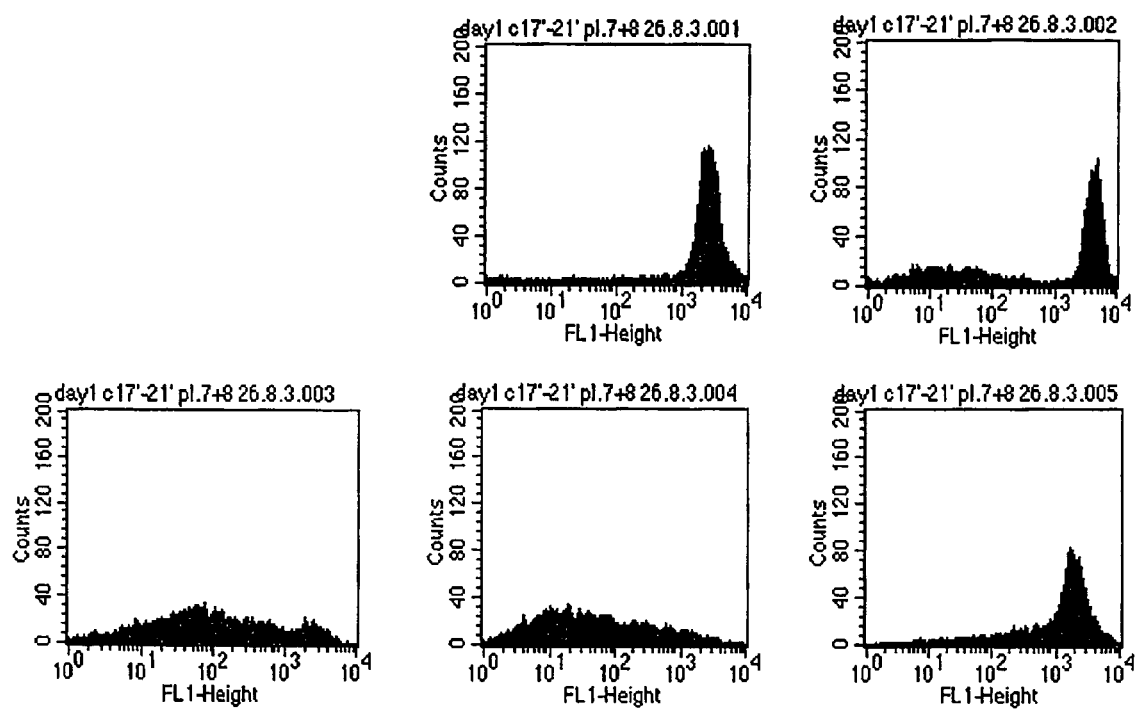
Figure 14:
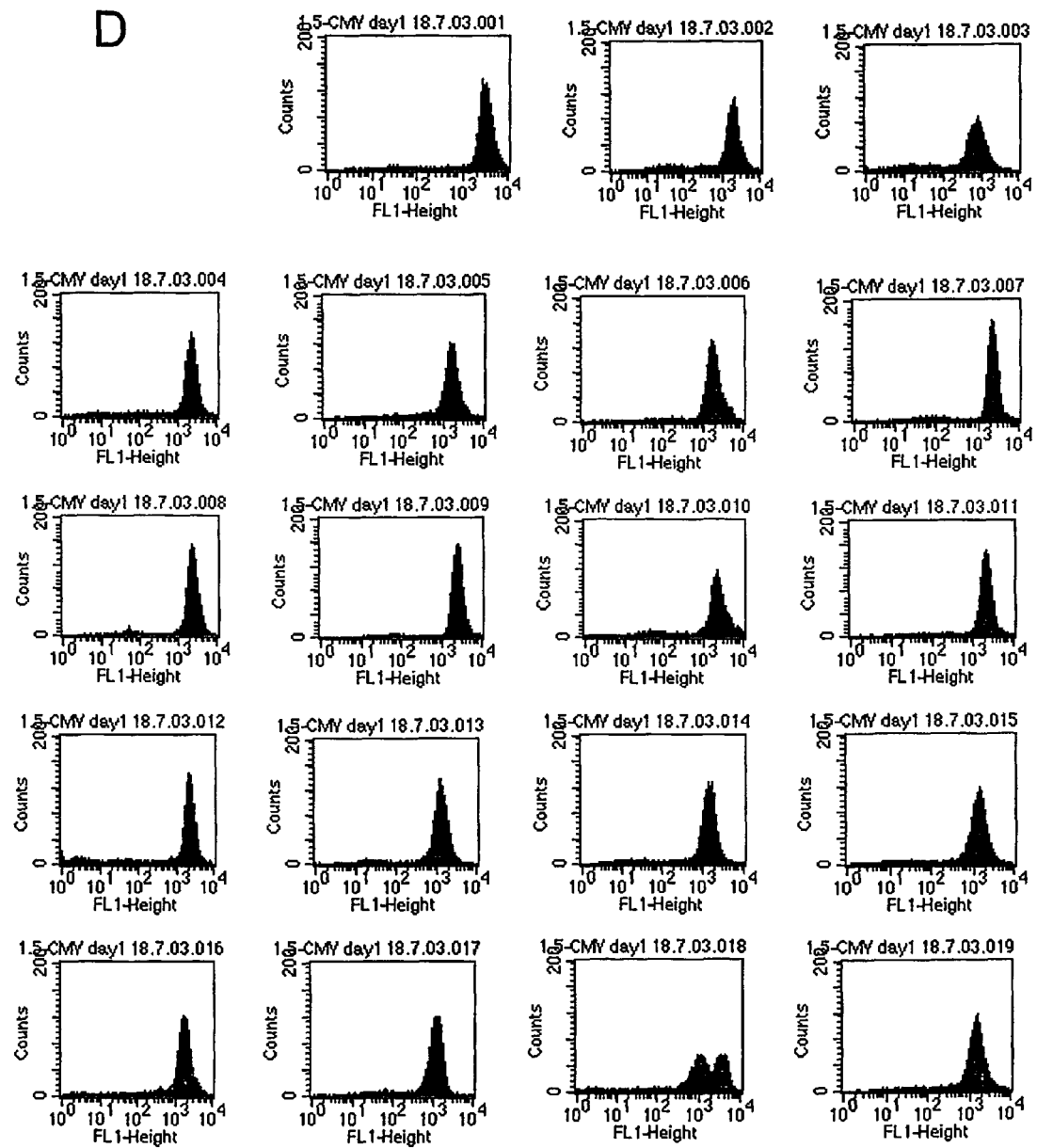
Figure 14:
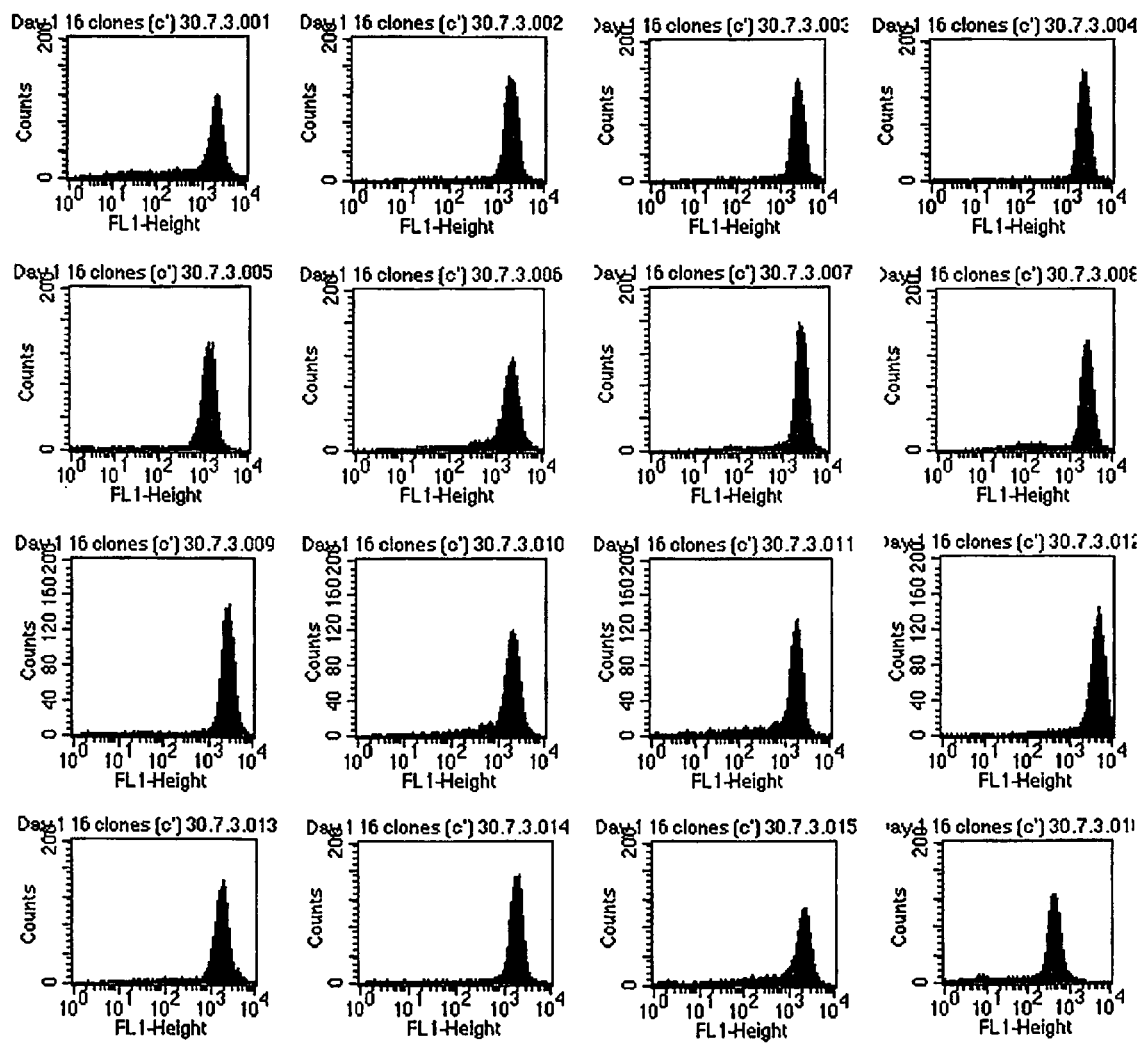

FIG. 14 shows that the 1.5 kb UCOE increases the consistency of GFP expression both with and between retrovirally transduced HeLa cell clones. FACS-sorted HeLa clones were expanded to 6-well size and GFP expression was analysed. (A-C) Histograms for all CMV clones. (D-E) Histograms for all 1.5UCOE-CMV clones.

Figure 15:
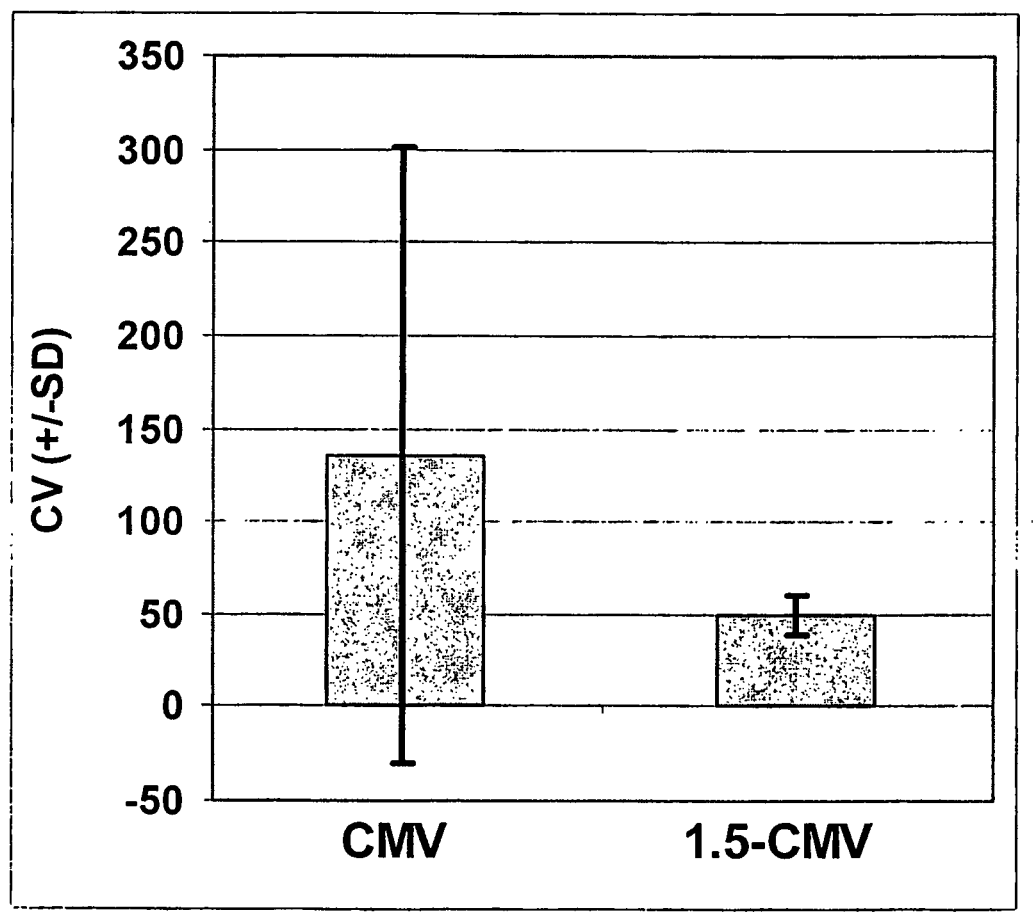

FIG. 15 shows that the 1.5 kb UCOE decreases the coefficient of variation (CV) of GFP expression in HeLa cell clones. Shown is the average CV value (+/−SD) of the means for all the retrovirally transduced and FACS-sorted HeLa clones from FIG. 5. Both the CV and its standard deviation (SD) of the 1.5UCOE-CMV clones are significantly decreased compared to the CMV clones.

EXAMPLES

Example 1

A 1.5 kb HP-1/hnRNP A2 UCOE Enhances Expression

Materials and Methods
Construction of Vectors

As discussed in our earlier application WO 00/05393, vector CET20 was generated by cloning an 8.3 kb HindIII fragment of the human HP-1/hnRNP A2 locus (which contains the HP1/RNP promoters and the extended CpG island) into pBluescript (Stratagene).

A 4186 bp (referred to as 4 kb) fragment of the insert was then removed by digestion with BamHI and HindIII. This fragment was end filled using T4 DNA polymerase and ligated into pEGFPN-1 (Clontech) that had been digested with AseI and end filled again using T4 DNA polymerase. Clones were then isolated with the fragment in both orientations.

The 1546 bp Esp3I (isoschizomer of BsmBI) fragment (referred to as the 1.5 kb fragment) was again isolated from CET20 by digestion with Esp3I (BsmBI) followed by end filling, this was then ligated into the AseI site of pEGFPN-1 as described above and clones identified with the fragment in both orientations (the 'forward' orientation being with the RNPA2 promoter oriented in the same 5' to 3' direction as the adjacent downstream operative CMV promoter from which the EGFP transgene was transcribed)

Transfection

CHO-K1 cells were transfected and selected in G418 according to standard methods and as described in the co-pending applications incorporated by reference.

Analysis of GFP Expression

Transfected cells were maintained on G418 selection at 600 μg/ml. Cells washed with standard phosphate buffered saline and stripped from the substrate with trypsin/EDTA according to standard methods. An excess of Nutrient mixture F12 (HAM) medium (Gibco) was added and the cells transferred to 5 ml round bottom polystyrene tubes for analysis by Becton Dickinson FACScan. GFP fluorescence was detected and compared with the autofluorescence of the parental cell population. Expression in the cell population was expressed as both median fluorescence expressed as arbitrary units set relative to the control (according to standard methods) on a linear scale in the Figures, and in terms of % cells judged as positive expressors.

Results

As shown in FIG. 3, the 1.5 kb fragment gave significant enhancement of expression as compared with the control (approximately 10-fold over at least 70 days) in terms of median fluorescence and about 60% of the enhancement seen with the 4 kb fragment, when inserted in the forward orientation. In the experiment shown in FIG. 5, expression from the forward 1.5 kb fragment is comparable with that obtained with the 4 kb fragment. However, the reverse orientation appears to be rather less effective in terms of median fluorescence, as shown in FIG. 3.

FIG. 4 shows both orientations to be comparable in terms of % positive cells. Nevertheless, these data suggest that this fragment may have a degree of directionality and that, for most purposes, the forward orientation is preferable.

Example 2

A 1kb HP-1/hnRNP A2 UCOE Enhances Expression

Materials and Methods
Construction of Vectors

The 1 kb UCOE containing vector was constructed by digesting the pEGFPN-1 vector with the 1.5 kb Esp3I fragment in the forward orientation with PciI and BspEI to remove the 5' 500 bp, followed by end filling and re-ligation. This generated a vector with the 987 bp BspEI-Esp3I fragment in one orientation only.

Results

The 1 kb (987 bp) fragment in the forward orientation appears comparable with the 1.5 kb fragment in the forward orientation in terms both of median fluorescence (FIG. 5) and % positive cells (FIG. 6).

Example 3

A 1.5 kb HP-1/hnRNP A2 UCOE Enhances Expression in an Adenovirally Encoded Construct Material and Methods
Cell Culture HeLa were obtained from ATCC (Manassas, Va.). PER.C6 were obtained from Crucell, (Leiden, The Netherlands). All purchased cell lines were cultured as recommended by the supplier. 911 cells were kindly provided by Prof. L. S. Young (Cancer Research UK Institute for Cancer Studies, University of Birmingham, Birmingham, UK) and were cultured in DMEM/10% FCS containing antibiotics.

Plasmid Construction

Figure 1:
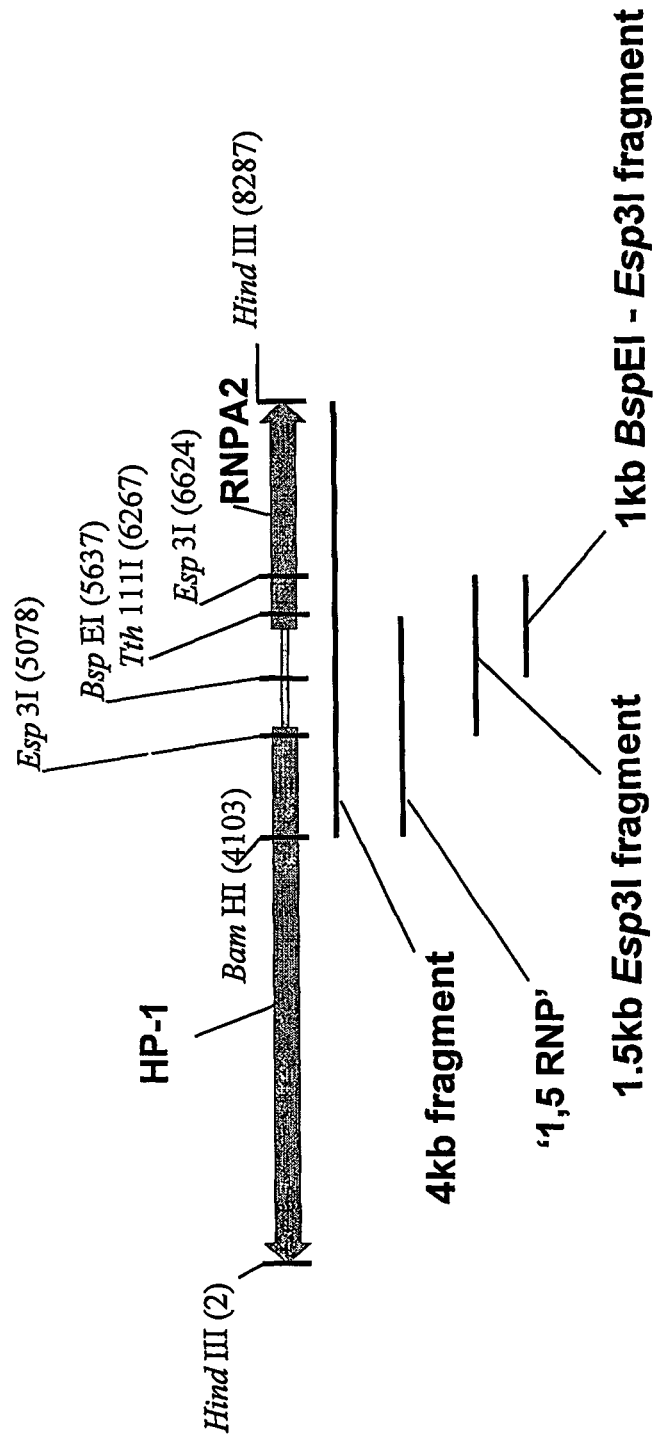
FIG. 1 shows a map of HP-1/hnRNPA2 locus indicating BamHI, HindIII, Esp3I, Tth111I and BspEI restriction sites defining various 4, 2, 1.5 and 1 kb CpG island fragments.

PGL3basic was obtained from Promega (Madison, Wis., USA) and contains the Luciferase-SV40p(A) cassette downstream from the multiple cloning site. The human CMV enhancer/promoter (0.9 kb) was cloned into SmaI digested pGL3basic to generate pGL3/CMV-Luc-SV40p(A). To generate pGL3/1.5 kb(F)UCOE-CMV-SV40p(A) the 1.5 kb UCOE Esp3I fragment (see FIGS. 1 and 2) was blunted with T4 DNA polymerase (NEB, Beverly, Mass., USA) and then ligated into NheI digested and T4 blunted pGL3basic/CMV-Luc.

Viral Vector Construction

To construct pPS1128/CMV-Luc-SV40p(A) and pPS1128/1.5 kb(F)UCOE-CMV-Luc-SV40p(A), the expression cassette were cut out from pGL3/CMV-Luc-SV40p(A) by PvuI/NheI/BamHI digest and from pGL3/1.5 kb (F)UCOE-CMV-Luc-SV40p(A) by KpnI/BamHI digest, both cassettes were then blunted and cloned into SpeI digested and blunted pPS1128 (Djeha et al., Cancer Gene Therapy 2000: 721-731). Plasmids were analysed by restriction enzyme digests.

The viruses Ad.CMV-Luc-SV40p(A) and Ad. 1.5 kb(F) UCOE-CMV-Luc-SV40p(A) were constructed by homologous recombination in PER.C6 using pPS1128/CMV-Luc-SV40p(A) and pPS1128/1.5 kb(F)UCOE-CMV-Luc-SV40p(A), respectively, and the overlapping adenoviral backbone vector pPS1160 (Djeha et al., Cancer Gene Therapy 2000: 721-731), scaled up and CsCl-purified and titered as described elsewhere (Lipinski et al., Gene Therapy, 8, 2001: 274-281).

Virus Infections and Luciferase Activity Assay

HeLa cells ($5.0 \times 10^4$ per 6-well) were infected in suspension with the respective virsues in 200 µl infection medium (EMEM/1% FCS containing antibiotics) for 2-3 hours. Then 1 ml complete medium was added and cells were seeded into 6-well plates. Whole cells extracts were prepared by lysing the cells in 200 µl lysis buffer (10 mM Sodium phosphate pH 7.8, 8 mM $MgCl_2$, 1 mM EDTA, 1% Triton-X-100, 15% Glycerol) and clearing the lysate by centrifugation (1 min 13,000×g, RT). An aliquot of each supernatant was assayed for luciferase activity in the linear range using a luminometer (Lumat LB 9501, Berthold, Wildbad, Germany) at the indicated time points.

Results

To analyse whether the UCOE can boost gene expression in an adenoviral vector the 1.5 kb UCOE was cloned in a forward orientation upstream (RNP promoter has the same orientation as the CMV promoter) of the human CMV enhancer/promoter driving a luciferase reporter gene. FIG. 7 shows schematically the structure of the two viruses that were compared for their luciferase activity. HeLa cells were infected at an MOI of 50 with the respective viruses and luciferase activity was analysed 2 days after infection. FIG. 8 shows clearly that the 1.5 kb UCOE fragment can dramatically increase the level of reporter gene expression in HeLa cells. To exclude a specific effect associated with the viral preparations we prepared new preparations of both viruses and repeated the experiments. FIG. 9 shows that the UCOE effect was not dependent on the viral preparation and was fully reproducible with the new, independent preparations.

Example 4

A 1.5 kb HP-1/hnRNP A2 UCOE Enhances Expression in a Retrovirally Encoded Construct Material and Methods
Cell Culture HeLa, CHO-K1 and 293 were obtained from ATCC (Manassas, Va.). HeLa and 293 were both cultured in DMEM, 10% FCS adding 1% NEAA and containing antibiotics. CHO-K1 were cultured in nutrient mix F12 (HAM) medium containing 10% FCS and antibiotics.

Plasmid Construction

The plasmids pVPack-GP and pVPack-VSV-G were obtained from Stratagene (LaJolla, Calif., USA) and express retroviral gag-pol and envelope VSV-G proteins, respectively. The retroviral vector pQCXIX was obtained from BD Bioscience and it contains the human CMV promoter for transgene expression (Palo Alto, Calif., USA). The plasmid phrGFP-1 was obtained from Stratagene and was used as source for a modified GFP cDNA. To clone pQCXIX-CMV-hrGFP the hrGFP cDNA was cut out from phr-GFP-1 by BamHI/EcoRV digest and cloned into BamHI/EcoRV digested pQCXIX. To generate pQCXIX-1.5UCOE-CMV-hrGFP, the 1.5 kb UCOE fragment (Esp3I/BsmBI fragment) was cloned as a blunted fragment into XbaI digested and blunted pQCXIX-CMV-hrGFP.

Production of Amphotroic, VSV-G-Enveloped Retrovirus Particles

All viruses were pseudotyped with the amphotropic VSV-G (Vesicular stomatitis virus Glycoprotein) envelope enabling highly effective and broad host range transduction. The retroviral vector used (pQCXIX) generates self-inactivating viruses due to a deletion in the U3 region of the 3' LTR which is copied to the 5' LTR after reverse transcription and therefore inhibits any further transcription from the 5'LTR.

$4.5 \times 10^6$ 293 cells (next day cells should be 80-90% confluent) were seeded in collagenase type I coated 8.4 cm diameter (55.6 $cm^2$) dishes the day before transient transfection. The next day 114 µl Lipofectamine 2000 (Invitrogen, Groenningen, The Netherlands) was mixed with 286 µl OptiMEM (Invitrogen) and incubated for 5 min at room temperature (RT). In parallel, 1.5 µg of each plasmid pVPack-GP, pVPack-VSV-G and retroviral vector was mixed with Opti-MEM to give a final volume of 400 µl. The DNA mix was added to the Lipofectamine 2000 solution and incubated for 20-30 min at RT. During this incubation the 293 cells were washed once with PBS and 6 ml OptiMEM/10% FCS was added to the cells. Finally the DNA/Lipofectamine mix was added dropwise to the cells and the cells were incubated in a 5% CO2 incubator at 37° C. for 5 hours. The medium was then replaced by 8 ml fresh 293 culture medium and the cells were incubated for a further 24-36 hours. Finally, supernatant containing the viral particles was harvested from the cells, centrifugated for 5 min at 1000 RPM to pellet cells and cell debris, and the supernatant was filter sterilized using Millex-HV PVDF low protein binding 0.45 µm filters (Millipore, Molsheim, France). The supernatant was aliquoted, snap frozen with liquid nitrogen and stored at -80° C.

Retroviral Transduction of Target Cell Lines

Target cells (HeLa, CHO-K1) were seeded at $1 \times 10^5$ cells/well in 6-well plates the day before infection. For viral transduction, different amounts of virus containing supernatant were added in the presence of 8.0 µg/ml polybrene (Sigma, St. Louis, Mo., USA). Cells were incubated with the virus for 24 hours and the medium was then replaced by fresh medium. Gene expression can be observed from two days post transduction. To prevent multiple copy per cell effects, for all analyses target cells were infected with a virus amount that resulted in much less than 100% transduction efficiency (normally giving 1-20% GFP-positive cells). Within this range of transduction efficiency, the volume of supernatant used for infection correlates linearly with the number of positive cells whereas the mean expression level shows a much lower increase.

FACS Analysis

For FACS analysis target cells were washed with PBS, trypsinized and resuspended in complete medium and hrGFP (green fluorescent protein) expression was analysed with a Becton Dickinson FACScan (BD, Franklin Lakes, N.J., USA) using constant instrument settings for each study. Data were analysed with CellQuest software for Apple McIntosh.

FACS Sorting

To sort GFP expressing HeLa and CHO-K1 cells, cells were prepared as for FACS analysis and then sorted with a BD Bioscience FACS-Sorter (kindly provided by The Institute for Cancer Studies, University of Birmingham, UK). Sorted single clones and pools were then expanded and GFP expression was followed up over time.

Results

In a first study CHO-K1 cells were transduced with cellular supernatants containing the retroviruses CMV-hrGFP (CMV) and 1.5UCOE-CMV-hrGFP (1.5UCOE-CMV). CHO-K1 cells were transduced as described in Material and Methods and three days after infection GFP-positive cells were FACS-sorted as a population pool (36,000 cells for each viral constructs) and then expanded. GFP expression and histogram pattern were followed over time and are illustrated in FIGS. 10 A and B, respectively. On day 17 of analysis the mean value for the 1.5UCOE-CMV pool is 2.6-fold higher than the mean from the CMV pool. Additionally, as the histograms show in FIG. 10B, the 1.5UCOE-CMV pool gives a tighter peak of GFP expression than the CMV pool. The average CV value (coefficient of variation; this is a marker for the homogeneity of GFP expression) for the GFP-positive cells in Marker 1 is 146.0 for the CMV pool and 83.0 for 1.5UCOE-CMV pool.

Comparable to this study CHO-K1 were transduced and the population was followed up over time without FACS-sorting. The MOI was chosen to give relatively low percentage of positive cells to exclude multiple copy per cell effects. As shown in FIG. 11A (pool I with about 5% GFP-positive cells), the mean of the positive cells for the 1.5UCOE-CMV population at the last time point of measurement is 2.8-fold higher than the mean of the CMV population. For pool II (about 15-25% GFP-positive cells; FIG. 12A), the mean for the 1.5UCOE-CMV population at the latest time point of measurement is 2.3-fold higher than the mean for the CMV population.

Comparable to the FACS-sorted population, the 1.5UCOE-CMV populations give a clearly tighter peak of expression compared to the CMV populations at all time points analysed (FIG. 11B and FIG. 12B).

As for CHO-K1, pools of 10,000 HeLa cells stably transduced with the retroviral constructs were FACS-sorted. In FIG. 13A the mean GFP value is shown including the mean value at the day of FACS-sorting (day—5). At the last time of measuring the mean of the 1.5UCOE-CMV pool is 1.6-fold higher than the mean of the CMV pool. As illustrated by the histograms in FIG. 13B, many of the CMV cells loose their high GFP expression level over time; in contrast most of the 1.5UCOE-CMV cells retain their high GFP expression.

HeLa single cell clones were also FACS-selected and expanded into 6-well plates. The CMV clones tend to give slightly higher peak expression than the 1.5UCOE-CMV clones, however, consistency of expression level, both within a clone and between clones, is significantly increased by the presence of the UCOE as indicated by the histograms for the all the analysed clones (FIG. 14 A-E). FIG. 15 shows the average coefficient of GFP expression variation (CV) and its standard variation (SD). The CV+/−SD value for the CMV clones is 135.0+/−165.3 and for the 1.5UCOE-CMV clones 49.4+/−10.9.

The invention claimed is:
1. An isolated polynucleotide comprising:
a) an extended methylation-free CpG island;
b) an expressible open reading frame, operably linked to said extended methylation-free CpG island;
c) a promoter, operably-linked to said open reading frame, wherein said promoter is not naturally linked to said CpG island;
wherein said CpG island is not more than 2 kb in size and comprises the sequence set forth in SEQ ID NO:1 or SEQ ID NO:2, and wherein reproducible expression of said open reading frame is obtained in the presence of the CpG island.

2. A polynucleotide according to claim 1, wherein SEQ ID NO:2 comprises a 987 bp BspE1-Esp3I restriction fragment.

3. A vector comprising the polynucleotide of any of claim 1 or 2.

4. A vector according to claim 3 wherein the vector is an integrating vector.

5. A vector according to claim 3 wherein the vector is a plasmid.

6. A vector according to claim 3 wherein the operably linked open reading frame is a therapeutic nucleic acid.

7. A vector according to claim 3, comprising any of SEQ ID NOs 1 or 2, a CMV promoter, a multiple cloning site, a polyadenylation sequence and genes encoding selectable markers under suitable control elements.

8. A host cell comprising the polynucleotide of any of claim 1 or 2.

9. A pharmaceutical composition comprising the polynucleotide according to any of claim 1 or 2 in combination with a pharmaceutically acceptable excipient.

10. A method for obtaining a desired gene product comprising expressing the polynucleotide according to any of claim 1 or 2 in a cell culture system in order to obtain a desired gene product, wherein the open reading frame encodes the desired gene product.

11. A method for increasing the expression of an endogenous gene comprising inserting the polynucleotide comprising SEQ ID NO 1 or 2 into the genome of a cell in a position operably associated with the endogenous gene thereby increasing the level of expression of the gene.

12. An isolated polynucleotide comprising:
a) an extended methylation-free CpG island;
b) an expressible open reading frame, operably linked to said extended methylation-free CpG island;
c) a promoter, operably-linked to said open reading frame, wherein said promoter
is not naturally linked to said CpG island;
wherein said CpG island is not more than 2 kb in size and comprises the sequence set forth in SEQ ID NO:2, and wherein reproducible expression of said open reading frame is obtained in the presence of the CpG island.

13. An isolated polynucleotide comprising:
a) an extended methylation-free CpG island;
b) an expressible open reading frame, operably linked to said extended methylation-free CpG island;
c) a promoter, operably-linked to said open reading frame, wherein said promoter is not naturally linked to said CpG island;
wherein said CpG island is not more than 2 kb in size and comprises the sequence set forth in SEQ ID NO:1, and wherein reproducible expression of said open reading frame is obtained in the presence of the CpG island.

* * * * *